US006955821B2

(12) United States Patent
Davis et al.

(10) Patent No.: US 6,955,821 B2
(45) Date of Patent: Oct. 18, 2005

(54) SUSTAINED RELEASE FORMULATIONS OF GUAIFENESIN AND ADDITIONAL DRUG INGREDIENTS

(75) Inventors: Robert D. Davis, Arlington, TX (US); Ralph W. Blume, Fort Worth, TX (US); Donald Jeffrey Keyser, Southlake, TX (US)

(73) Assignee: Adams Laboratories, Inc., Fort Worth, TX (US)

( * ) Notice: Subject to any disclaimer, the term of this patent is extended or adjusted under 35 U.S.C. 154(b) by 21 days.

(21) Appl. No.: 10/121,706

(22) Filed: Apr. 15, 2002

(65) Prior Publication Data

US 2003/0049318 A1 Mar. 13, 2003

Related U.S. Application Data

(63) Continuation-in-part of application No. 09/559,542, filed on Apr. 28, 2000, now Pat. No. 6,372,252.

(51) Int. Cl.[7] .............................. A61K 9/20; A61K 9/22; A61K 9/26; A61K 9/48; A61K 9/52
(52) U.S. Cl. ........................ 424/468; 424/451; 424/452; 424/457; 424/458; 424/464; 424/465; 424/469
(58) Field of Search ................................. 424/451, 452, 424/457, 458, 464, 465, 468, 469, 400, 439, 453, 472, 474, 489, 490; 514/849, 850, 962, 963

(56) References Cited

U.S. PATENT DOCUMENTS

| 3,065,143 A | 11/1962 | Christenson et al. |
| 3,362,880 A | 1/1968 | Sampson |

(Continued)

FOREIGN PATENT DOCUMENTS

| EP | 0409781 B1 | 6/1994 |
| GB | 2255344 A | 11/1992 |
| WO | WO 87/00044 | 1/1987 |
| WO | WO 98/22097 | 5/1998 |

OTHER PUBLICATIONS

Coated Pharmaceutical Dosage Forms, Bauer et al, MedPharm Scientific Publishers (1998), p. 83.*
Welling, P.G., "Oral Controlled Drug Administration: Pharmacokinetic Considerations, " Drug Dev. Ind. Pharm., 9, 1185–1225 (1983).
Kim, C., "Pharmacokinetic Considerations in the Design of Controlled Release Dosage Forms," Controlled Release Dosage Form Design, ch. 11 (Technomic Publishing Co., Inc. 2000).
Bodmeier, R. et al., "Prolonged Release Multiple–Unit Dosage Forms Based On Water–Soluble Cellulosic Polymers or Aqueous Latexes," Proceed. Intern. Sump. Control. Rel. Bioact. Mater., 18 (1991), Controlled Release Society, Inc.

*Primary Examiner*—Thurman K. Page
*Assistant Examiner*—S. Tran
(74) *Attorney, Agent, or Firm*—Hunton & Williams LLP

(57) ABSTRACT

The invention relates to a novel pharmaceutical sustained release formulation of guaifenesin and at least one additional drug ingredient. The formulation may comprise a hydrophilic polymer, preferably a hydroxypropyl methylcellulose, and a water-insoluble polymer, preferably an acrylic resin, in a ratio range of about one-to-one (1:1) to about nine-to-one (9:1), more preferably a range of about three-to-two (3:2) to about six-to-one (6:1), and most preferably in a range of about two-to-one (2:1) to about four-to-one (4:1) by weight. This formulation capable of providing therapeutically effective bioavailability of guaifenesin for at least twelve hours after dosing in a human subject. The invention also relates to a modified release product which has two portions: a first portion having an immediate release formulation of guaifenesin and a second portion having a sustained release formulation of guaifenesin, wherein one or both portions has at least one additional drug ingredient. The modified release product has a maximum guaifenesin serum concentration equivalent to that of an immediate release guaifenesin tablet, and is capable of providing therapeutically effective bioavailability of guaifenesin for at least twelve hours after dosing in a human subject.

77 Claims, 18 Drawing Sheets

U.S. PATENT DOCUMENTS

| | | |
|---|---|---|
| 3,362,881 A | 1/1968 | Klaus et al. |
| 3,555,151 A | 1/1971 | Kaplan et al. |
| 3,870,790 A | 3/1975 | Lowey et al. |
| 3,981,984 A | 9/1976 | Signorino |
| 4,122,157 A | 10/1978 | Huber |
| 4,140,755 A | 2/1979 | Sheth et al. |
| 4,167,558 A | 9/1979 | Sheth et al. |
| 4,226,849 A | 10/1980 | Schor |
| 4,248,857 A | 2/1981 | DeNeale et al. |
| 4,248,858 A | 2/1981 | Guley et al. |
| 4,259,314 A | 3/1981 | Lowey |
| 4,309,404 A | 1/1982 | DeNeale et al. |
| 4,309,405 A | 1/1982 | Guley et al. |
| 4,357,469 A | 11/1982 | Schor |
| 4,369,172 A | 1/1983 | Schor et al. |
| 4,389,393 A | 6/1983 | Schor et al. |
| 4,424,235 A | 1/1984 | Sheth et al. |
| 4,540,566 A | 9/1985 | Davis et al. |
| 4,543,370 A | 9/1985 | Porter et al. |
| 4,680,323 A | 7/1987 | Lowey |
| 4,695,464 A | 9/1987 | Alderman |
| 4,699,779 A | 10/1987 | Palinczar |
| 4,704,285 A | 11/1987 | Alderman |
| 4,756,911 A * | 7/1988 | Drost et al. .................. 424/468 |
| 4,795,643 A | 1/1989 | Seth |
| 4,798,725 A | 1/1989 | Patel |
| 4,851,392 A | 7/1989 | Shaw et al. |
| 4,871,548 A | 10/1989 | Edgren et al. |
| 4,968,508 A | 11/1990 | Oren et al. |
| 4,980,170 A * | 12/1990 | Schneider et al. .......... 424/451 |
| 4,983,398 A | 1/1991 | Gaylord et al. |
| 4,994,276 A | 2/1991 | Baichwal et al. |
| 5,032,406 A * | 7/1991 | Dansereau et al. ......... 424/472 |
| 5,047,248 A | 9/1991 | Calanchi et al. |
| 5,098,715 A | 3/1992 | McCabe et al. |
| 5,133,974 A * | 7/1992 | Paradissis et al. .......... 424/480 |
| 5,164,398 A | 11/1992 | Sims et al. |
| 5,200,193 A | 4/1993 | Radebaugh et al. |
| 5,286,493 A * | 2/1994 | Oshlack et al. ............. 424/468 |
| 5,292,534 A | 3/1994 | Valentine et al. |
| 5,326,571 A | 7/1994 | Wright et al. |
| 5,395,626 A | 3/1995 | Kotwal et al. |
| 5,403,593 A | 4/1995 | Royce |
| 5,427,799 A | 6/1995 | Valentine et al. |
| 5,445,829 A | 8/1995 | Paradissis et al. |
| 5,451,409 A | 9/1995 | Rencher et al. |
| 5,472,704 A | 12/1995 | Santus et al. |
| 5,494,681 A | 2/1996 | Cuca et al. |
| 5,593,694 A | 1/1997 | Hayashida et al. |
| 5,650,169 A | 7/1997 | Conte et al. |
| 5,656,296 A | 8/1997 | Khan et al. |
| 5,662,933 A | 9/1997 | Baichwal et al. |
| 5,780,057 A | 7/1998 | Conte et al. |
| 5,807,580 A | 9/1998 | Luber |
| 5,840,329 A | 11/1998 | Bai |
| 5,945,123 A * | 8/1999 | Hermelin .................... 424/464 |
| 5,968,554 A | 10/1999 | Beiman et al. |
| 6,210,710 B1 | 4/2001 | Skinner |
| 6,217,903 B1 | 4/2001 | Skinner |
| 6,372,252 B1 * | 4/2002 | Blume et al. ............... 424/464 |

\* cited by examiner

Guaifenesin Concetrations Following the Administration of 1200 mg Guaifenesin and 60 mg Dextromethorphan Hydrobromide to Normal Volunteers in Three Formulations
(Mean, Standard Error)

Dextromethorphan Plasma Concentrations Following the Administration of 1200 mg Guaifenesin and 60 mg Dextromethorphan Hydrobromide to Normal Volunteers in Three Formulations (Mean, Standard Error)

Dextrorphan Plasma Concentrations Following the Administration of 1200 mg Guaifenesin and 60 mg Dextromethorphan Hydrobromide to Normal Volunteers in Three Formulations
(Mean, Standard Error)

Plasma Guaifenesin Concentration Following Administration of 1200 mg Guaifenesin Along with 120 mg Pseudoephedrine HCl to Normal Volunteers (Mean, Standard Error)

Plasma Pseudoephedrine Concentration Following Administration of 120 mg Pseudoephedrine HCl along with 1200 mg Guaifenesin to Normal Volunteers
(Mean, Standard Error)

SUSTAINED RELEASE FORMULATIONS OF GUAIFENESIN AND ADDITIONAL DRUG INGREDIENTS

CROSS-REFERENCE TO RELATED APPLICATIONS

This application is a continuation-in-part of U.S. application Ser. No. 09/559,542 now U.S. Pat. No. 6,372,252 which was filed on Apr. 28, 2000 and issued on Apr. 16, 2002.

BACKGROUND OF THE INVENTION

1. Field of the Invention

The present invention is directed to a sustained release formulation for oral administration comprising guaifenesin and at least one drug ingredient and methods of manufacture thereof. In particular, the invention is directed to a sustained release formulation which maintains a therapeutically effective blood concentration of guaifenesin and at least one drug ingredient for a duration of at least twelve hours. The present invention further relates to a modified release bi-layer tablet containing guaifenesin and at least one drug ingredient which demonstrates a maximum serum concentration equivalent to an immediate release tablet yet maintains a therapeutically effective blood concentration of guaifenesin for a duration of about twelve hours.

2. Description of Related Art

Sustained release pharmaceutical formulations provide a significant advantage over immediate release formulations to both clinicians and their patients. Sustained release dosage forms are administered to patients in much fewer daily doses than their immediate release counterparts and generally achieve improved therapeutic effect and efficiency in the fewer daily doses.

For example, in a standard dosage regimen a 400 mg immediate release dosage form of an active ingredient (hereinafter "drug" or "medicament") with a short half-life, such as guaifenesin, may have to be administered to a patient three times within 12 hours to maintain adequate bioavailability of the drug to achieve therapeutic effect. This results in a series of three serum concentration profiles in the patient in which there is a rapid increase of drug followed by a similar rapid decrease. Such rapid increases and decreases provide a patient with a short window of appropriate blood concentration of the medicament for optimum therapy. A 1200 mg sustained release dosage form, on the other hand, may only have to be administered to a patient once every 12 hours to achieve therapeutic effect. Sustained release dosage forms generally control the rate of active drug absorption, so as to avoid excessive drug absorption while maintaining effective blood concentration of the drug to provide a patient with a consistent therapeutic effect over an extended duration of time.

Besides reducing the frequency of dosing and providing a more consistent therapeutic effect, sustained release dosage forms generally help reduce side effects caused by a drug. Because sustained release dosage forms deliver the drug in slow, incremental amounts versus the cyclic high and low concentrations of immediate release formulations, it is easier for a patient's body to digest the drug, thereby avoiding undesirable side-effects. For patients who self-administer therapies, sustained release dosage forms generally result in greater compliance due to the lower frequency of dosing, lower quantity of dosage units to be consumed, and reduced undesired side-effects.

Sustained release formulations for the sequential or timed release of medicaments are well known in the art. Generally, such formulations contain drug particles mixed with or covered by a polymer material, or blend of materials, which is resistant to degradation or disintegration in the stomach and/or in the intestine for a selected period of time. Release of the drug may occur by leeching, erosion, rupture, diffusion or similar actions depending upon the nature of the polymer material or polymer blend used.

Conventionally, pharmaceutical manufacturers have used hydrophilic hydrocolloid gelling polymers such as hydroxypropyl methylcellulose, hydroxypropyl cellulose, or Pullulan to formulate sustained release tablets or capsules. These polymers first form a gel when exposed to an aqueous environment of low pH thereby slowly diffusing the active medicament which is contained within the polymer matrix. When the gel enters a higher pH environment such as that found in the intestines, however, it dissolves resulting in a less controlled drug release. To provide better sustained release properties in higher pH environments, some pharmaceutical manufacturers use polymers which dissolve only at higher pHs, such as acrylic resins, acrylic latex dispersions, cellulose acetate phthalate, and hydroxypropyl methylcellulose phthalate, either alone or in combination with hydrophilic polymers.

Generally, these formulations are prepared by combining the medicament with a finely divided powder of the hydrophilic polymer, or the hydrophilic and water-insoluble polymers. These ingredients are mixed and granulated with water or an organic solvent and the granulation is dried. The dry granulation is then usually further blended with various pharmaceutical additives and compressed into tablets.

Although these types of formulations have been successfully used to manufacture dosage forms which demonstrate sustained release properties, these formulations generally do not have the desired release profile or serum concentration of medicament over an extended period of time. These sustained release formulations generally result in a delay in the appearance of drug in the blood stream, thereby delaying therapeutic effect. Additionally, when the drug does appear, its maximum serum concentration ($C_{max}$) is lower than the maximum concentration required for the most effective therapeutic result. Furthermore, most formulations which claim twelve hour potency release almost all of their drug within six to eight hours, making the formulation less therapeutically effective towards the end of the twelve hour period. To prevent blood serum concentrations of active drug from falling below a therapeutically effective level at extended time periods, many manufacturers increase the drug strength of the dosage form. The increase in drug strength, however, results in a concomitant increase in side-effects.

To improve the release profile of certain sustained release dosage forms, some pharmaceutical manufacturers have made tablets and capsules which comprise a combination of an immediate release formulation and a sustained release formulation. Although this solution improves the $C_{max}$ and length of time before the drug appears in the blood stream in some formulations, the extended therapeutic effect is not improved.

Furthermore, every medicament has different solubility properties and pH dependencies which affect its dissolution rate, and hence its bioavailability. Bioavailability can also be affected by a number of factors such as the amounts and types of adjuvants used, the granulation process, compression forces (in tablet manufacturing), surface area available for dissolution and environmental factors such as agitation in the stomach and the presence of food. Due to these numerous factors, specific formulations play an important role in the preparation of prolonged action solid dosage forms, particularly in the preparation of solid dosage forms which achieve appropriate bioavailability for optimum therapeutic effect.

Guaifenesin is known chemically as 3-(2-methoxyphenoxy)-1,2-propanediol. It is an expectorant, a drug which increases respiratory tract fluid secretions and helps to loosen phlegm and bronchial secretions. By reducing the viscosity of secretions, guaifenesin increases the efficiency of a cough reflex and of ciliary action in removing accumulated secretions from trachea and bronchi. Guaifenesin is readily absorbed from the intestinal tract and is rapidly metabolized and excreted in urine. Guaifenesin has a typical plasma half-life of approximately one hour. Because of the rapid metabolization and excretion of guaifenesin, typical immediate release dosage tablets of guaifenesin provide only a short window of therapeutic effectiveness for patients resulting in the various recognized problems described above.

None of the prior art has described a sustained release dosage form of guaifenesin which is capable of sustaining therapeutic effective for at least twelve hours. Likewise, none of the prior art has described a sustained release dosage form of guaifenesin which has a $C_{max}$ equivalent to that of an immediate release formulation, appears in the blood stream as quickly as an immediate release formulation, yet sustains therapeutic effect for at least twelve hours.

SUMMARY OF THE INVENTION

The present invention overcomes the problems and disadvantages associated with current strategies and designs in formulations of modified release guaifenesin dosage forms.

This invention relates to a novel sustained release pharmaceutical formulation comprising guaifenesin and at least one drug ingredient. The sustained release formulation may comprise a combination of at least one hydrophilic polymer and at least one water-insoluble polymer. The total weight ratio of hydrophilic polymer to water-insoluble polymer may be in a range of about one-to-one (1:1) to about nine-to-one (9:1), more preferably in a range of about three-to-two (3:2) to about six-to-one (6:1), and most preferably in a range of about two-to-one (2:1) to about four-to-one (4:1). When a tablet comprising the sustained release formulation is exposed to an aqueous medium of low pH, such as that found in the stomach, the polymer combination gels causing guaifenesin and the drug ingredient to diffuse from the gel. When the tablet passes to the intestines where an aqueous medium of higher pH is present, the gel begins to dissolve, thereby releasing guaifenesin and the drug ingredient(s) in controlled amounts. The tablet is capable of releasing therapeutically effective amounts of guaifenesin over an extended period, i.e. twelve or more hours and at least one additional drug ingredient immediately, over an extended period, or both.

This invention also encompasses a modified release composition which comprises two discrete portions (e.g. a bi-layer tablet, or capsule), an immediate release formulation and a sustained release formulation. Each formulation comprises a specific quantity of guaifenesin and may optionally contain at least one additional drug. The immediate release formulation is formulated to dissolve in aqueous acidic medium, such as that found in the stomach, to quickly release guaifenesin contained within the portion, and optionally quickly release the at least one additional drug ingredient. The sustained release portion may comprise a combination of hydrophilic polymer and a water-insoluble polymer in a ratio range of about one-to-one (1:1) to about nine-to-one (9:1), more preferably a range of about three-to-two (3:2) to about six-to-one (6:1), and most preferably from about two-to-one (2:1) to about four-to-one (4:1).

The present invention also relates to sustained release preparations of the type described above in the form of capsules having beads or granules of both immediate release formulation and beads or granules of sustained release formulation. Alternatively, the sustained release formulation may comprise a core that is coated by a layer of the immediate release formulation to form a single tablet. For purpose of illustration only, the invention will be described in detail in the context of the bi-layered tablet embodiment.

The bi-layer tablet of the present invention demonstrates a maximum serum concentration ($C_{max}$) and time of availability in the blood stream that are equivalent to an immediate release tablet. The bi-layer tablet also provides sustained release of guaifenesin over at least a twelve hour period from one dose. The bi-layer tablet of the present invention further maintains serum concentration levels of guaifenesin at a therapeutically effective level for at least a twelve hour period without an increase in the drug strength of the dosage form. As the bi-layer tablet of the present invention also contains at least one additional drug ingredient, the additional drug ingredient can be formulated within the sustained release formulation, immediate release formulation, or both. In one embodiment, the bi-layer tablet of the present invention maintains serum concentration levels of at least one additional drug at a therapeutically effective level for at least a twelve hour period without an increase in the drug strength of the dosage form.

The present invention also relates to methods of manufacturing sustained release formulations and bi-layer tablets of the present invention. An example of a manufacturing method for a sustained release formulation comprises mixing a hydrophilic polymer and active ingredients in a mixer, adding water to the mixture and continuing to mix and chop, drying the mixture to obtain hydrophilic polymer encapsulated granules, milling and screening the resulting granulation, and blending it with various pharmaceutical additives, additional hydrophilic polymer, and water insoluble polymer. The formulation may then be tableted and may further be film coated with a protective coating which rapidly dissolves or disperses in gastric juices.

An example of a bi-layer tablet manufacturing method comprises blending a quantity of guaifenesin and optionally, at least one drug ingredient with various excipients, colorants, and/or other pharmaceutical additives to form an immediate release formulation, separately blending another quantity of guaifenesin and at least one drug ingredient with a hydrophilic polymer, a water-insoluble polymer, and various excipients, colorants, and/or other pharmaceutical additives to form a sustained release formulation, and compressing a quantity of the immediate release formulation with a quantity of the sustained release formulation to form a bi-layer tablet. The tablet may then be optionally coated with a protective coating which rapidly dissolves or disperses in gastric juices.

Other objects, advantages and embodiments of the invention are set forth in part in the description which follows, and in part, will be obvious from this description, or may be learned from the practice of the invention.

DETAILED DESCRIPTION OF THE INVENTION

Figure 1:
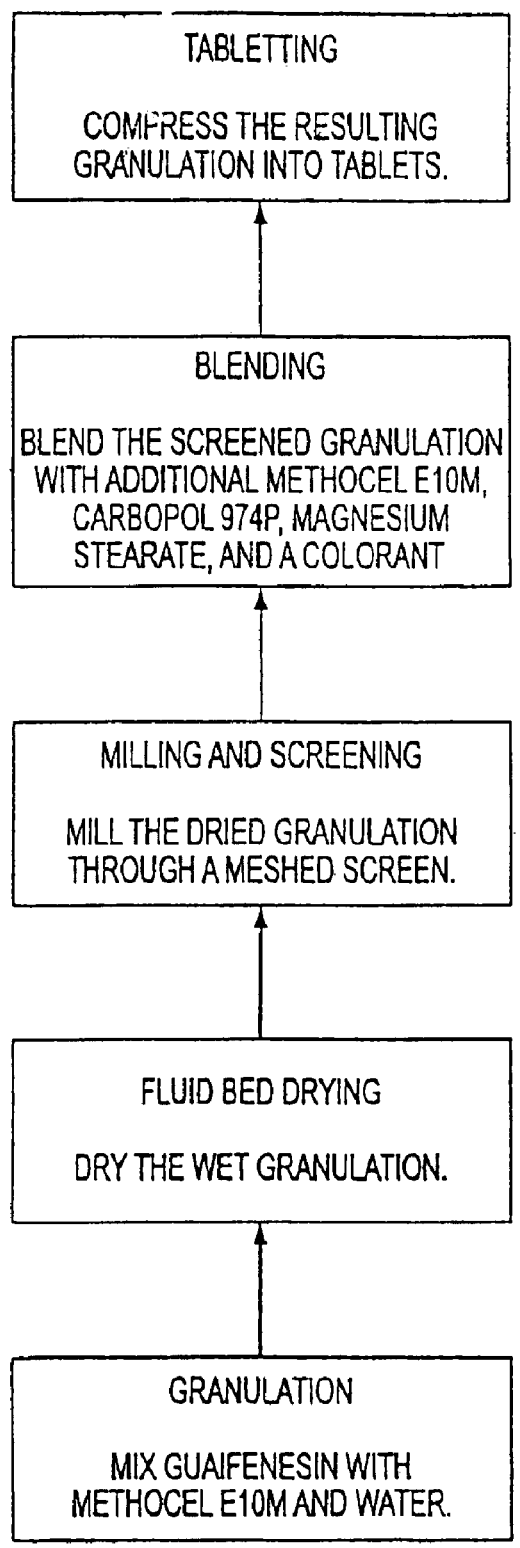
FIG. 1 is a flow diagram depicting steps in a wet granulation method for manufacturing the sustained release formulation of the present invention.
Figure 2:
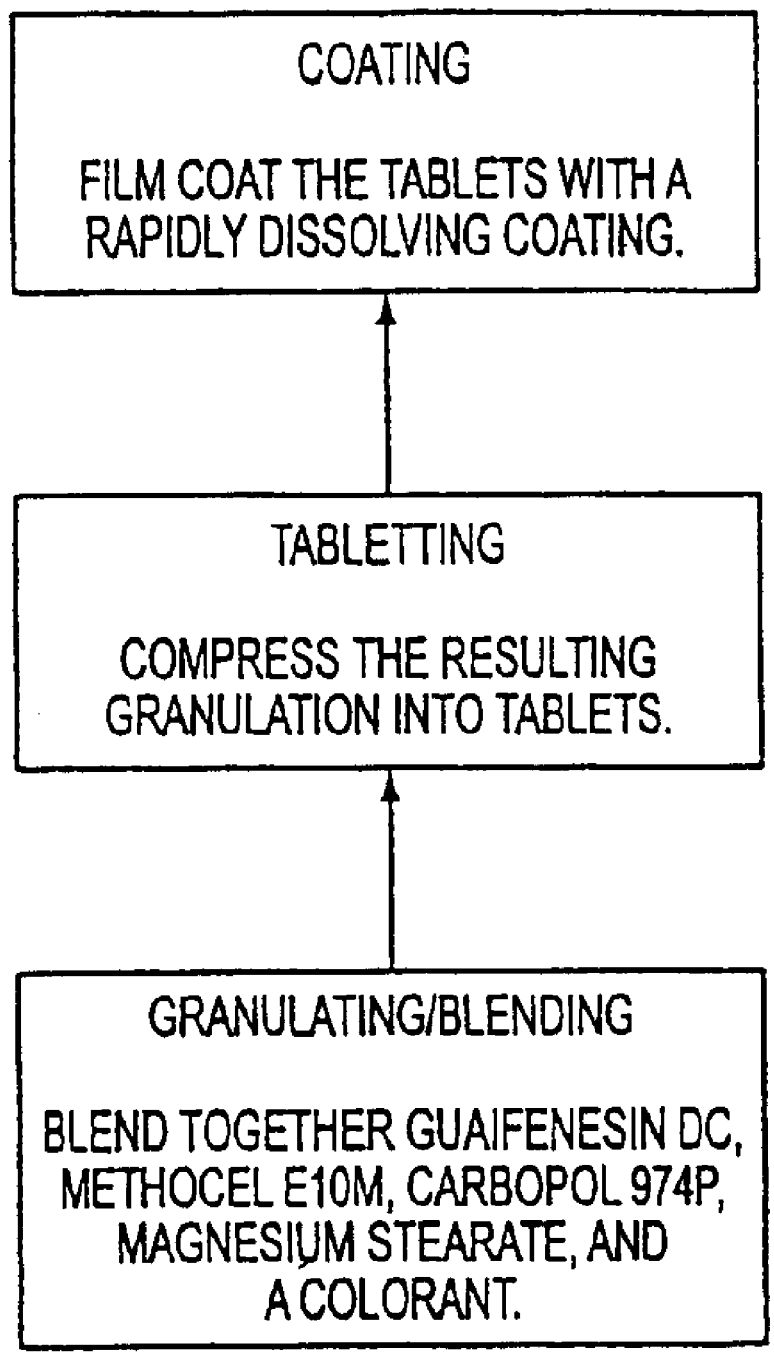
FIG. 2 is a flow diagram depicting steps in a dry granulation method for manufacturing the sustained release formulation of the present invention.
Figure 3:
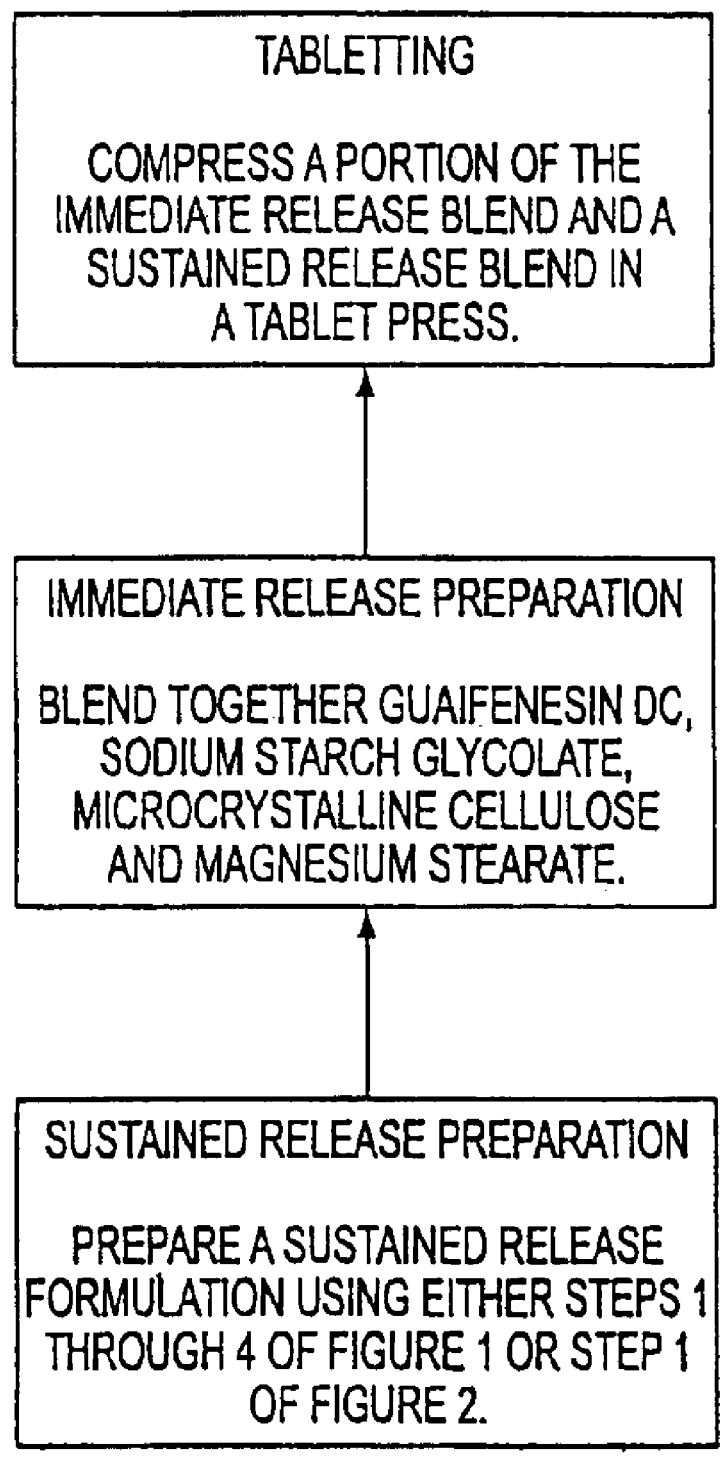
FIG. 3 is a flow diagram depicting steps in a method for manufacturing the bi-layer tablet of the present invention.

The present invention encompasses a novel sustained release formulation comprising guaifenesin and at least one additional drug ingredient. This invention also encompasses a modified release composition which comprises two discrete portions, an immediate release formulation and a sustained release formulation. Each formulation comprises a specific quantity of guaifenesin and may optionally contain at least one additional drug. The immediate release formulation is formulated to dissolve in aqueous acidic medium, such as that found in the stomach, to quickly release guaifenesin contained within the portion, and optionally quickly release the at least one additional drug ingredient. In a preferred embodiment, the sustained release formulation comprises a combination of a hydrophilic polymer and a water-insoluble polymer in a ratio range of about one-to-one (1:1) to about nine-to-one (9:1), more preferably a range of about three-to-two (3:2) to about six-to-one (6:1), and most preferably in a range of about two-tone (2:1) to about four-to-one (4:1).

The present invention also relates to sustained release preparations of the type described above in the form of bi-layered tablets or capsules having a combination of beads or granules of immediate release formulation and beads or granules of sustained release formulation. Alternatively, the sustained release formulation may comprise a core that is coated by a layer of immediate release formulation to form a single tablet. For purpose of illustration only, the invention will be described in detail in the context of the bi-layered tablet embodiment. When the embodiment is a bi-layered tablet, the tablet is made of two portions: one portion comprising a sustained release formulation and a second portion comprising an immediate release formulation. In a preferred embodiment, the at least one additional drug ingredient can be present within the sustained release formulation, the immediate release formulation, or both depending upon the desired effect.

1. Sustained Release Formulation

In one embodiment of the present invention, a sustained release formulation comprises guaifenesin and at least one drug ingredient both mixed with a polymer blend which comprises at least one hydrophilic polymer and at least one water-insoluble polymer. In a further embodiment, the sustained release formulation may comprise a combination of guaifenesin and at least one additional drug ingredient, wherein the additional drug ingredient includes, but not limited to, an antitussive such as dextromethorphan hydrobromide, codeine, hydrocodone, a decongestant such as phenylephrine hydrochloride, phenylpropanolamine hydrochloride, pseudoephedrine hydrochloride or ephedrine, an antihistamine such as chlorpheniramine maleate, brompheniramine maleate, phenindamine tartrate, pyrilamine maleate, doxylamine succinate, phenyltoloxamine citrate, diphenhydramine hydrochloride, promethazine, and clemastine fumerate, an analgesic such as aspirin, ibuprofen, naprosin, and acetaminophen, or combinations thereof. Preferably, the drug ingredient is dextromethorphan hydrobromide, pseudoephedrine hydrochloride, or a combination thereof.

Hydrophilic polymers suitable for use in the sustained release formulation include: one or more natural or partially or totally synthetic hydrophilic gums such as acacia, gum tragacanth, locust bean gum, guar gum, or karaya gum, modified cellulosic substances such as methylcellulose, hydroxomethylcellulose, hydroxypropyl methylcellulose, hydroxypropyl cellulose, hydroxyethylcellulose, carboxymethylcellulose; proteinaceous substances such as agar, pectin, carrageen, and alginates; and other hydrophilic polymers such as carboxypolymethylene, gelatin, casein, zein, bentonite, magnesium aluminum silicate, polysaccharides, modified starch derivatives, and other hydrophilic polymers known to those of skill in the art or a combination of such polymers.

These hydrophilic polymers gel and dissolve slowly in aqueous acidic media thereby allowing the guaifenesin and at least one drug ingredient to diffuse from the gel in the stomach. When the gel reaches the intestines, it dissolves in controlled quantities in the higher pH medium, where the guaifenesin and the drug ingredient are fairly absorbable, to allow sustained release of guaifenesin and at least one drug ingredient throughout the digestive tract. Preferred hydrophilic polymers are the hydroxypropyl methylcelluloses such as those manufactured by The Dow Chemical Company and known as METHOCEL ethers. In one preferred embodiment of a sustained release formulation the hydrophilic polymer is a METHOCEL ether known as METHOCEL E10M.

Water-insoluble polymers which are suitable for use in the sustained release formulation are polymers which generally do not dissolve in solutions of a pH below 5, and dissolve more slowly in basic solutions than the hydrophilic polymer. Because the polymer is insoluble in low pH environments such as those found in gastric fluid, it aids in retarding drug release in those regions. Likewise, because the polymer dissolves more slowly in solutions, of higher pH than hydrophilic polymers, it aids in retarding drug release throughout the intestines. This overall delayed release results in a more uniform serum concentration of guaifenesin.

The water-insoluble polymers suitable for use in this invention include: polyacrylic acids, acrylic resins, acrylic latex dispersions, cellulose acetate phthalate, polyvinyl acetate phthalate, hydroxypropyl methylcellulose phthalate, and other polymers common to those of skill in the art. In a preferred embodiment, a sustained release formulation comprises the acrylic resin CARBOPOL 974P supplied by BF Goodrich.

A sustained release formulation of the present invention may further comprise pharmaceutical additives including, but not limited to: lubricants such as magnesium stearate, calcium stearate, zinc stearate, powdered stearic acid, hydrogenated vegetable oils, talc, polyethylene glycol, and mineral oil; colorants such as Emerald Green Lake and various FD&C colors; binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quarternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art. Colorants include, but are not limited to, Emerald Green Lake, FD&C Red #40, FD&C Yellow #6, FD&C Yellow #10, or FD&C Blue #1. In one preferred embodiment, a sustained release formulation further comprises magnesium stearate and Emerald Green Lake. In another preferred embodiment, a sustained release formulation further comprises magnesium stearate and FD&C Blue #1 Aluminum Lake Dye.

A sustained release formulation of the present invention can comprise at least two drug ingredients, at least one hydrophilic polymer, at least one water-insoluble polymer, and at least one pharmaceutical additive in any appropriate percent quantity which permits dissolution of drug ingredients that results in a therapeutically effective serum concentration profile for a full twelve hours. In a preferred embodiment, a sustained release formulation comprises from about 75% to about 95% guaifenesin by weight, from about 1% to about 15% by weight of a additional drug ingredient, from about 1% to about 10% hydroxypropyl methylcellulose, from about 0.5% to about 2.5% acrylic resin, from about 0.4% to about 1.5% magnesium stearate, and from about 0.01% to about 1% colorant by weight. In a more preferred embodiment, a sustained release formulation comprises from about 80% to about 90% guaifenesin by weight, from about 3% to about 10% by weight of a additional drug ingredient, from about 2% to about 5% hydroxypropyl methylcellulose, from about 1% to about 1.5% acrylic resin, from about 0.7% to about 1% magnesium stearate, and from about 0.03% to about 0.13% colorant by weight.

The present inventive sustained release formulation controls release of guaifenesin and at least one additional drug ingredient into the digestive tract slowly over time. The drug guaifenesin experiences a shift in water solubility as the pH of the environment in which it resides (i.e. stomach versus intestinal tract) changes. In a more acidic environment, such as that found in the stomach, guaifenesin is less soluble while in a higher pH environment, such as that found in the intestines, guaifenesin is readily soluble. Dissolution rate of guaifenesin throughout the digestive tract is thus of primary importance in determining concentrations of guaifenesin attained in the blood and tissues as a drug formulation is digested.

To maintain a blood concentration of guaifenesin which provides good therapeutic effect, the release, or dissolution, of guaifenesin from a formulation matrix is preferably retarded and/or controlled through the intestines. The combination of hydrophilic and water-insoluble polymers of the sustained release formulation of the present invention gels when exposed to media of low pH. This creates a matrix out of which guaifenesin can diffuse. When the gelled polymer combination is exposed to media of a higher pH, the gel begins to slowly dissolve thereby releasing guaifenesin at a controlled rate.

Additionally, when at least one additional drug ingredient is present in the combination of hydrophilic and water-insoluble polymers of the sustained release formulation of the present invention, the additional drug ingredient diffuses from the gel when the combination gels when exposed to media of low pH. As discussed above, when the gelled polymer combination is exposed to media of a higher pH, the gel begins to slowly dissolve thereby releasing at least one additional drug ingredient at a controlled rate in addition to the guaifenesin. When using drug ingredients approved by the Food and Drug Administration (FDA), the sustained release formulation may be formulated to mimic the blood serum profile of the additional drug as described in the clinical documents filed with the FDA or as required by the FDA. In other words, the sustained release formulation releases at least one additional drug at a similar rate to the commercially available formulation, thereby providing a therapeutically effective amount of the additional drug.

In a preferred embodiment of the present invention, a sustained release formulation comprises a hydrophilic polymer and a water-insoluble polymer in a ratio of about one-to-one (1:1) to about nine-to-one (9:1), more preferably the range is about three-to-two (3:2) to about six-to-one (6:1), and most preferably the range of hydrophilic polymer to water-insoluble polymer is about two-to-one (2:1) to about four-to-one (4:1). In another embodiment, the sustained release formulation comprises not more than about 10% hydrophilic polymer, preferably, not more than 6%, and in a more preferred embodiment, the sustained release formulation comprises not more than 2.5% of the hydrophilic polymer by weight. In another preferred embodiment, the hydrophilic polymer is hydroxypropyl methylcellulose and the water-insoluble polymer is acrylic resin. The inventors have discovered that the ratios result in a serum concentration profile of guaifenesin that provides an optimal therapeutic concentration for at least twelve hours.

A sustained release formulation of the present invention may be manufactured according to any appropriate method known to those of skill in the art of pharmaceutical manufacture. In one embodiment, guaifenesin and a hydrophilic polymer may be mixed in a mixer with an aliquot of water to form a wet granulation. The granulation may be dried to obtain hydrophilic polymer encapsulated granules of guaifenesin. The resulting granulation may be milled, screened, then blended with various pharmaceutical additives, water insoluble polymer, and additional hydrophilic polymer. The formulation may then tableted and may further be film coated with a protective coating which rapidly dissolves or disperses in gastric juices.

A preferred embodiment of a method of preparing a sustained release formulation of the present invention may comprise loading approximately 126 kg of GUAIFENESIN and about 2 kg of METHOCEL E10M into a high shear mixer. The METHOCEL E10M and GUAIFENESIN may be mixed for about seven minutes at a mixing speed of about 150 RPM and a chopper speed of about 2000 RPM. The mixing and chopping speeds may then be increased to about 200 RPM and 3000 RPM respectively for about five minutes while about 49 kg of water are added to the mixer contents. The mixer may be run for two additional minutes to complete granulation. In a further preferred embodiment, the shut off for the mixer load is set to 21 kilowatts.

The wet granulation may be emptied into a fluid bed bowl and placed into a fluid bed dryer set to a dryer air flow of 900 CFM and an inlet temperature of about 50° C. to about 55° C. until the outlet temperature increases at a rate of 1° per minute. The air flow may then be decreased to 600 CFM, and the inlet temperature may be decreased to 43° C. until the granulation is dried to a moisture content of no more than 0.5%. In another preferred embodiment, the outlet temperature is set to a cut-off of 48° C. In yet another preferred embodiment, an agitator in the fluid bed bowl may be run intermittently during drying. The dried granulation may be passed through a mill fitted with a suitable screen size so that not more than about 30% of the resulting granulation comes through a 100 mesh screen and not more than about 10% of the resulting granulation is retained on a 10 mesh screen. In one preferred embodiment, the dried granulation may be passed through a mill fitted with a 0.109" size screen at a mill speed of about 500 to about 1500 RPM and a screw feed rate of about 35 to about 45 RPM. The resulting screened granulation is about 95% GUAIFENESIN and is called GUAIFENESIN DC (Direct Compressed) herein after. Screened granulation may be transferred to a 10 cubic foot V blender, combined with about another 0.6 kg of METHOCEL E10M, about 0.3 kg of a colorant such as Emerald Green Lake or FD&C BLUE #1, about 0.7 kg of magnesium stearate, and about 1.3 kg of CARBOPOL 974P. The combination may be blended for about three minutes.

In another preferred embodiment of a method of preparing a sustained release formulation of the present invention may comprise loading about 101 kg to about 150 kg of GUAIFENESIN, about 4.5 kg to about 18 kg of the additional drug ingredient, about 4.5 kg to about 5 kg of METHOCEL E10M, about 1.5 kg to about 2.25 kg of CARBOPOL® 974P, and about 40 g to about 240 g of colorant into a high shear mixer. If at this time water is to be added, then about 1 kg to about 1.5 kg of magnesium stearate is added as well. The ingredients may be mixed for about ten to about 12 minutes at a mixing speed of about 150 RPM and a chopper speed of about 2000 RPM. The mixing and chopping speeds may then be increased to about 200 RPM and 3000 RPM, respectively, for about five minutes while optionally about 29 kg of water are added to the mixer contents. If no water is added, then from about 1 kg to about 1.5 kg of magnesium stearate can be added at this time. The mixer may be run for ten additional minutes to complete granulation. In a further preferred embodiment, the shut off for the mixer load is set to 21 kilowatts.

The wet granulation may be emptied into a fluid bed bowl and placed into a fluid bed dryer set to a dryer air flow of 900 CFM and an inlet temperature of about 38° C. to about 48° C. until the outlet temperature increases at a rate of 1° C. per minute. The air flow may then be decreased to 600 CFM, and the inlet temperature may be decreased to 43° C. until the granulation is dried to a moisture content of no more than 0.5%. In another preferred embodiment, the outlet temperature is set to a cut-off of 48° C. In yet another preferred embodiment, an agitator in the fluid bed bowl may be run intermittently during drying. The dried granulation may be passed through a mill fitted with a suitable screen size so that not more than about 30% of the resulting granulation comes through a 100 mesh screen and not more than about 10% of the resulting granulation is retained on a 10 mesh screen. In one preferred embodiment, the dried granulation may be passed through a mill fitted with a size screen of about 0.109" to about 0.125" at a mill speed of about 500 to about 1500 RPM and a screw feed rate of about 35 to about 45 RPM.

The resulting formulations may further be compressed on a tablet compressor machine using tooling to form tablets. The tablets may be any appropriate weight, size, and shape depending on the desired dosage strength of tablet. In one embodiment, these tablets may further be loaded into a coating pan and film coated with Opadry Y-S-3-714 (supplied by Colorcon, Inc.) and air dried in the pan.

Another embodiment of the method of preparing a sustained release formulation of the present invention may comprise blending the drug ingredients, hydrophilic polymer, water insoluble polymer, and any pharmaceutical additives. The resulting blend may then be compressed into tablets and, if desired, film coated with a protective coating which rapidly dissolves or disperses in gastric juices. In a preferred embodiment of such a method, about 126 kg of GUAIFENESIN DC (about 95% purity), about 2.6 kg of METHOCEL E10M, about 1.3 kg of CARBOPOL 974P and about 0.333 kg of a colorant such as Emerald Green Lake or FD&C BLUE #1 may be loaded into a 10 cubic foot V Blender. The ingredients may be blended for about 20 minutes at which time about 0.6 kg of magnesium stearate may be added to the blended ingredients. This mixture may be blended for about another 10 minutes. The resulting formulation may further be compressed on a tablet compressor machine using tooling to form tablets. The tablets may be any appropriate weight, size, and shape depending on the desired dosage strength of the tablet. These tablets may further be loaded into a coating pan and film coated with Opadry Y-S-3-714 (supplied by Colorcon, Inc.) and air dried in the pan.

Figure 4:
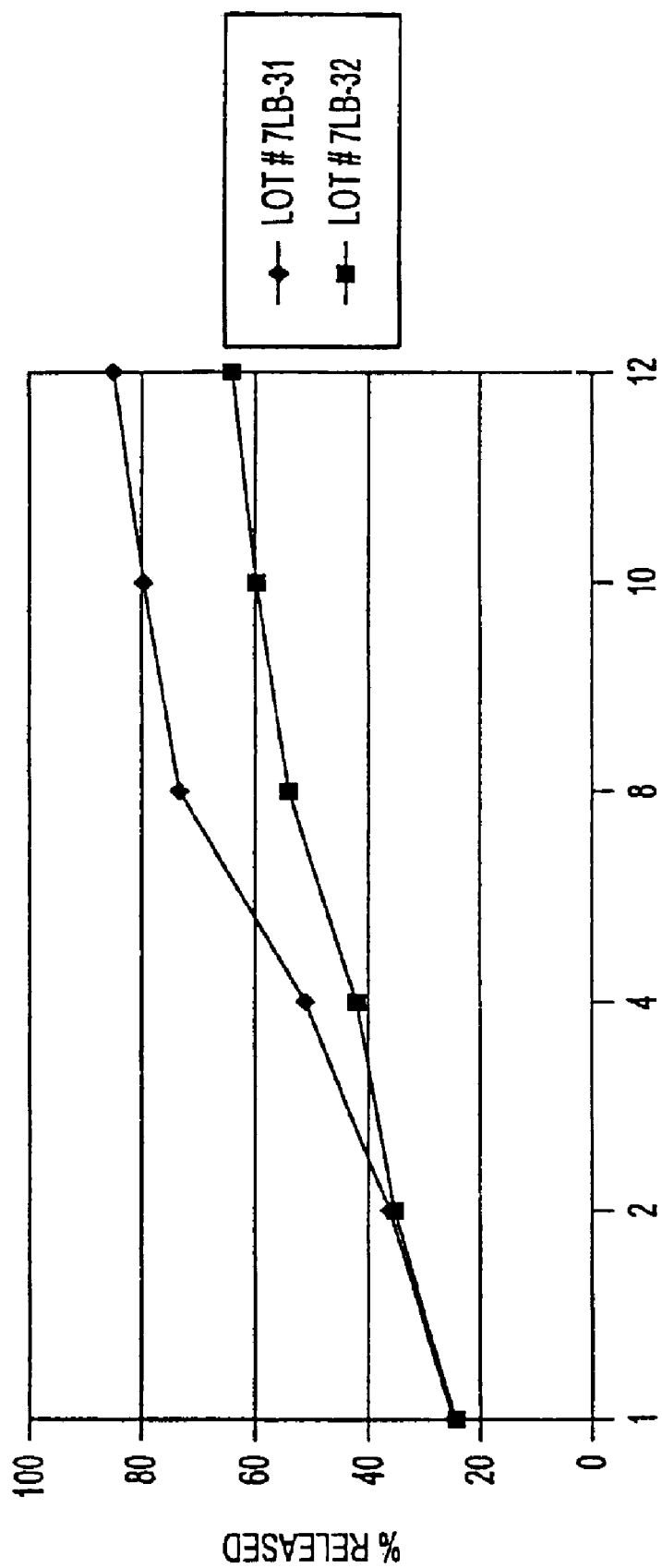
FIG. 4 is a graph demonstrating the dissolution profiles of tablets comprising two different sustained release formulations of the present invention.

Tablets comprising a sustained release formulation of the present invention were prepared and tested for both in vitro and in vivo release characteristics as described in Examples 1, 2, and 3 below. In the in vitro testing, the dissolution rates of these tablets were compared against modified release tablets formulated without acrylic resin (Example 1), and three commercially available tablets, one being an immediate release formulation and the other two being modified release formulations. Tablets comprising the sustained release formulation of the present invention demonstrated a slower, more controlled release of guaifenesin over a twelve hour period than any of the other tablets (see Example 1 and 2, and FIGS. 4 and 5).

Figure 6:
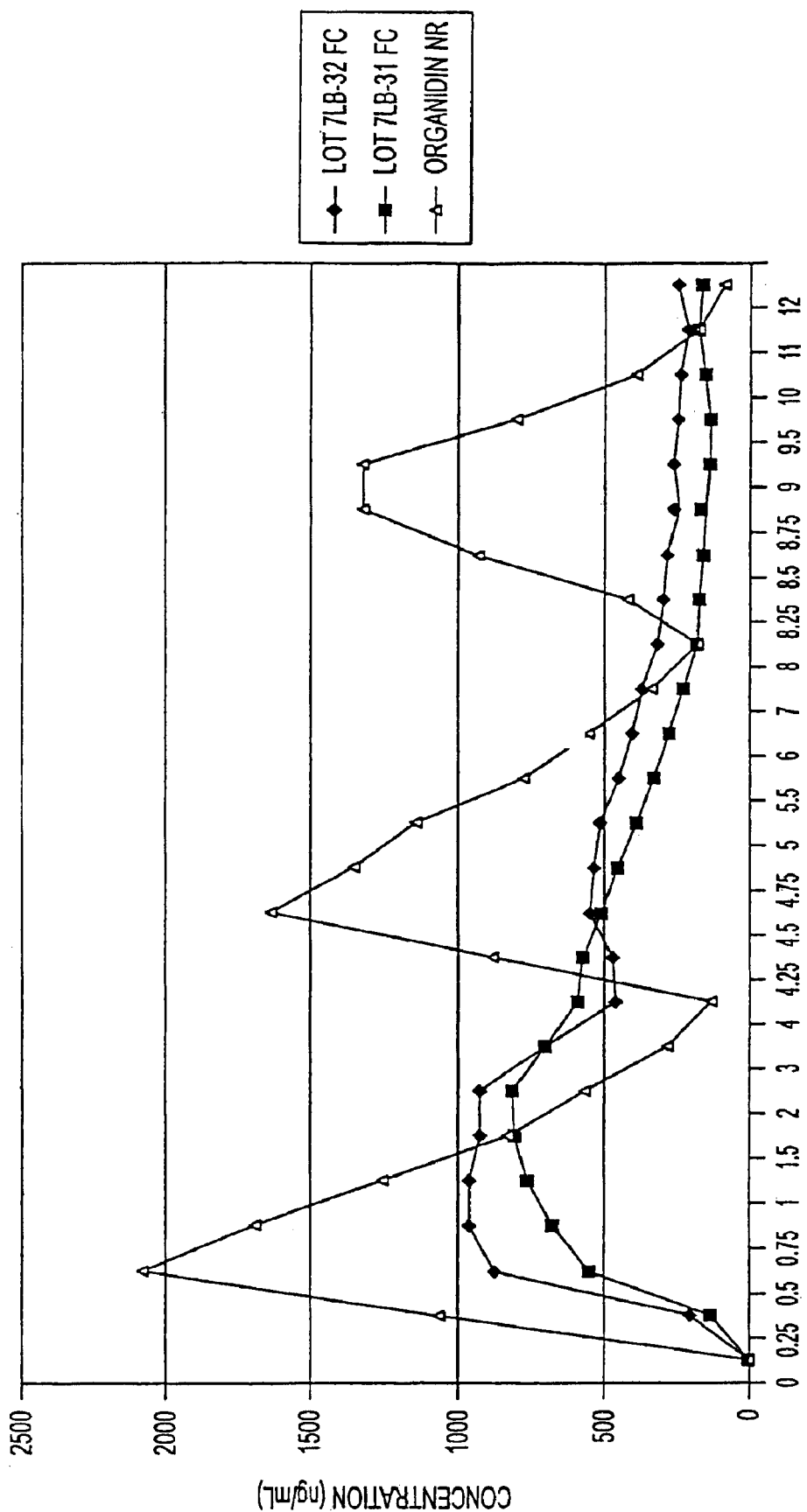
FIG. 6 is a graph demonstrating the plasma concentration of guaifenesin over time in healthy human volunteers who were dosed with three different guaifenesin formulations; an immediate release formulation known in the art, and two different sustained release formulations of the present invention.

In the in vivo testing, serum concentrations of subjects taking tablets comprising the sustained release formulation of the present invention were compared with serum concentrations of subjects taking immediate release guaifenesin tablets and modified release guaifenesin tablets formulated without acrylic resin (see Example 3 and FIG. 6). Tablets comprising the sustained release formulation of the present invention demonstrated improved sustained release and therapeutic concentration at extended time periods that the other two formulations. However, in the subjects taking tablets comprising the sustained release formulation of the present invention, it took longer for guaifenesin to appear in the blood stream and the maximum serum concentration ($C_{max}$) of guaifenesin in these subject was less than half of that of the subjects taking the immediate release tablets.

2. Modified Release Product

To improve the $C_{max}$ and speed of appearance of guaifenesin in patients while maintaining therapeutic effect for at least twelve hours, a portion of a sustained release formulation of the present invention as described above may be combined with a portion of an immediate release formulation in a modified release product. In a preferred embodiment, at least one additional drug ingredient can be present within the sustained release formulation, the immediate release formulation, or both depending upon the desired effect. When using drug ingredients approved by the Food and Drug Administration (FDA), the sustained release formulation, immediate release formulation, or both may be formulated to mimic the blood serum profile of the additional drug as described in the clinical documents filed with the FDA or as required by the FDA. In other words, the sustained and/or immediate release formulations of the modified release product may release the at least one additional drug at a similar rate to the commercially available formulation, thereby providing a therapeutically effective amount of the additional drug.

The modified release product can be in the form of bi-layered tablets, capsules having a combination of beads or granules of immediate release formulation and sustained release formulation, or a tablet wherein the sustained release formulation comprises a core that is coated by a layer of the immediate release formulation. For purpose of illustration only, the invention will be described in detail in the context of the bi-layered tablet embodiment.

The immediate release formulation may comprise guaifenesin and various pharmaceutical additives such as lubricants, colorants, binders, glidants, surface active agents, preservatives, stabilizers, as described above and/or any other pharmaceutical additives known to those of skill in the art. In one embodiment, the immediate release layer comprises at least one drug ingredient. In another embodiment, the immediate release layer comprises at least two drug ingredients. In a more preferred embodiment, an immediate release formulation comprises guaifenesin, microcrystalline cellulose, sodium starch glycolate, and magnesium stearate. In another more preferred embodiment, an immediate release formulation comprises guaifenesin, at least one drug ingredient, microcrystalline cellulose, hydroxypropyl methylcellulose, sodium starch glycolate, and magnesium stearate. In yet another preferred embodiment, an immediate release formulation may comprise about 47% to about 58% guaifenesin, about 32% to about 42% microcrystalline cellulose, about 3% to about 8% sodium starch glycolate, and about 0.3% to about 0.5% magnesium stearate by weight. In yet another preferred embodiment, an immediate release formulation may comprise about 47% to about 58% guaifenesin, about 3% to about 5% of at least one additional drug ingredient, about 32% to about 42% microcrystalline cellulose, about 2% to about 5% hydroxypropyl methylcellulose, about 3% to about 8% sodium starch glycolate, and about 0.3% to about 0.5% magnesium stearate by weight.

The bi-layer tablet may be manufactured according to any method known to those of skill in the art. The resulting tablet may comprise the two portions compressed against one another so that the face of each portion is exposed as either the top or bottom of the tablet, or the resulting tablet may comprise the sustained release portion in the center coated by the immediate release portion so that only the immediate release portion is exposed. In a preferred embodiment, a bi-layer tablet of the present invention comprises the two portions compressed against one another so that the face of each portion is exposed.

In a preferred method of manufacturing the bi-layer tablets of the present invention a sustained release formulation is prepared according to either a wet granulation or dry granulation method as described above. The immediate release formulation may be prepared by simply blending the guaifenesin with any pharmaceutical additives. If at least one additional drug ingredient is present, then water may be added to the formulation, as described above. In a further preferred embodiment, appropriate quantities of GUAIFENESIN DC, microcrystalline cellulose, and sodium starch glycolate are blended in a 10 cubic foot blender for about twenty minutes. An appropriate quantity of magnesium stearate is then added to the ingredients and blended for about ten more minutes to make an immediate release formulation. Portions of the sustained release formulation and immediate release formulation are then compressed by a tablet compressor machine capable of forming bi-layer tablets. In one embodiment, these tablets may further be coated with a protective film which rapidly disintegrated or dissolves in gastric juices.

The tablets may be made with any ratio of guaifenesin to at least one additional drug ingredient which results in a blood profile demonstrating appropriate therapeutic effect over extended time periods. As discussed above, the additional drug ingredient may be present in an amount sufficient to mimic the blood serum profile of the commercially available formulation of the drug and not to exceed the maximum dose approved by the FDA for the treatment, prevention, or amelioration of a particular illness or disease. In one embodiment, the ratio in the sustained release formulation of guaifenesin to at least one additional drug ingredient is about one point one-to-one (1.1:1) to about four-to-one (4:1) by weight, preferably, the ratio is about three-to-two (3:2) to about nine-to-one (9:1) by weight, and more preferably, the ratio of guaifenesin to at least one additional drug ingredient is about three-to-one (3:1) to about 20:1 by weight. When present in the immediate release layer, the amount of the at least one additional drug should be sufficient to match the drug release profile of the additional drug within the sustained release profile. Within this embodiment, the ratio in the immediate release formulation of guaifenesin to at least one additional drug ingredient, if present, is about four-to-one (4:1) to about one-to-one (1:1), preferably, the ratio is about nine-to-one (9:1) to about three-to-two (3:2), and more preferably, the ratio of guaifenesin to at least one additional drug ingredient is about nine-to-one (9:1) to about (12:1) by weight.

The tablets may be made with any ratio of sustained release to immediate release formulation which results in a blood profile demonstrating appropriate therapeutic effect over extended time periods. In one embodiment, the bi-layer tablets comprise guaifenesin distributed within the sustained release formulation and the immediate release formulation wherein the ratio of guaifenesin is about one-to-one (1:1) to about 49:1 by weight, preferably the ratio is about three-to-two (3:2) to about 19:1, and more preferably, the ratio of guaifenesin distributed within the sustained release formulation and the immediate release formulation is about five-to-one (5:1) to about nine-to-one (9:1) by weight, respectively. For example, in a 1200 mg bi-layer modified release guaifenesin tablet of the present invention, there may be about 200 mg of guaifenesin in the immediate release layer and about 1000 mg of guaifenesin in the sustained release layer.

The tablets may be made with at least one additional drug only within the sustained release formulation. Optionally, however, the tablets may be made with at least one additional drug distributed within the sustained release formulation and the immediate release formulation. In one embodiment, the bi-layer tablets comprise a additional drug ingredient distributed within the sustained release formulation and immediate release formulation wherein the ratio of additional drug ingredient is about one-to-one (1:1) to about 19:1 by weight, preferably the ratio is about three-to-two (3:2) to about nine-to-one (9:1), and more preferably the ratio of additional drug ingredient distributed within the sustained release formulation and the immediate release formulation is about three-to-one (3:1) to about four-to-one (4:1) by weight, respectively.

In one preferred embodiment of manufacturing a 1200 mg bi-layer sustained release guaifenesin tablet, about 105 kg of GUAIFENESIN DC, about 2.5 kg of METHOCEL E10M, about 1.25 kg of CARBOPOL 974P, and about 0.333 kg of Emerald Green Lake or FD&C BLUE #1 in a 10 cubic foot P.K. blender for about twenty minutes. About 0.6 kg of magnesium stearate may then be added and blending continued for about another ten minutes to prepare the sustained release formulation. Approximately 21 kg of GUAIFENESIN DC, approximately 11.75 kg of microcrystalline cellulose, and approximately 3 kg of sodium starch glycolate may be blended in a 3 cubic foot P.K. blender for about twenty minutes. Approximately 0.1 kg of magnesium stearate may then be added and blending continued for about another ten minutes to prepare the immediate release formulation. The two formulations may then be compressed to make bi-layer tablets wherein about 75% of each tablet may be sustained release formulation and about 25% if each tablet may be immediate release formulation. The tablets may be any dosage strength, size, or shape. In a preferred embodiment, 1200 mg tablets are round and about ⅝ inch in diameter, about 0.28 inch–0.31 inch in thickness, weigh about 1.46 grams and have a hardness range of about 15–40 SCU. In another preferred embodiment, 600 mg tablets are round and about ½ inch in diameter, about 0.218 inch–0.230 inch in thickness, weigh about 0.729 grams and have a hardness range of about 12–30 SCU.

In another preferred embodiment of manufacturing a 1200 mg bi-layer sustained release guaifenesin tablet, about 101 kg of GUAIFENESIN DC, about 4.5 kg of at least one additional drug ingredient such as dextromethorphan, about 5 kg of METHOCEL E10M, about 1.5 kg of CARBOPOL 974P, and about 0.04 kg of FD&C BLUE #1 are blended in a 10 cubic foot Day mixer for about twelve minutes. Thereafter, about 29 kg of water is added and the mixture is blended for an additional 10 minutes, followed by drying. About 1 kg of magnesium stearate may then be added and blending continued for about another ten minutes to prepare the sustained release formulation. About 45.6 kg of GUAIFENESIN, about 3.6 kg of at least one additional drug ingredient such as dextromethorphan, about 40.32 kg of microcrystalline cellulose, and approximately 3 kg of sodium starch glycolate are blended in a 3 cubic foot Day mixer for about 12 minutes. Thereafter, about 36 kg of water is added and the mixture is blended for an additional 10 minutes, followed by drying. About 0.48 kg of magnesium stearate may then be added and blending continued for about another ten minutes to prepare the immediate release formulation. The two formulations may then be compressed to make bi-layer tablets wherein about 75% of each tablet may be sustained release formulation and about 25% if each tablet may be immediate release formulation. The tablets may be any dosage strength, size, or shape. In a preferred embodiment, 1200 mg tablets are round and about ⅝ inch in diameter, about 0.31 inch–0.34 inch in thickness, weigh about 15.3 grams and have a hardness range of about 15–35 SCU. In another preferred embodiment, 600 mg tablets are round and about ½ inch in diameter, about 0.22 inch–0.26 inch in thickness, weigh about 7.65 grams and have a hardness range of about 15–65 SCU.

The immediate release portion of the bi-layer tablet is formulated to dissolve in aqueous media of low pH, such as that found in the stomach, to quickly release the guaifenesin contained within the portion. This results in rapid bioavailability of a high concentration of guaifenesin. As demonstrated in Example 6 and FIGS. 9 and 10 below, the immediate release portion of the bi-layer tablet results in a maximum serum concentration ($C_{max}$) and time of maximum serum concentration ($T_{max}$) equivalent to the $C_{max}$ obtained when the first of three doses of a standard immediate release formulation having one third the amount of guaifenesin is dosed every four hours over a 12 hour period.

The sustained release portion gels when exposed to media of low pH allowing the sustained release portion of the tablet to be passed into the intestinal tract. In the intestines, the gelled sustained release portion is exposed to media of a higher pH, causing the gel to slowly dissolve, thereby allowing guaifenesin to diffuse and dissolve out of the gelled matrix. This results in controlled bioavailability over an extended time period (i.e. twelve or more hours) causing the tablet to provide extended therapeutic effect. This result is evidenced in Example 6 and FIGS. 9 and 10 below—the half-life of the modified release bi-layer tablet is increased to more than 3 hours and the tablet has an $AUC_{inf}$ (the area under a plasma concentration versus time curve from time 0 to infinity) of greater than 8000 hr*ng/mL. As demonstrated in Example 7 and FIG. 11, the bi-layer tablets of the present invention had a further surprising result in that a 600 mg tablet had a $T_{max}$ equivalent to that of a 1200 mg and a $C_{max}$ and $AUC_{inf}$ approximately half of a 1200 mg tablet. Thus, without adjusting or changing the composition of the sustained release formulation or bi-layer tablet, a lower dosage strength guaifenesin tablet of the present invention exhibits plasma concentration profile that is approximately directly proportional to that of a higher dosage strength guaifenesin tablet also of the present invention. As further demonstrated in Example 7 and FIG. 11, the bi-layer tablets of the present invention had another surprising result in that the $C_{max}$ and $AUC_{inf}$ of a 1200 mg tablet administered to volunteers who had been fasting and the $C_{max}$ and $AUC_{inf}$ of a 1200 mg tablet administered to volunteers who had consumed a high fat meal were approximately equivalent. Thus, a bi-layer tablet of the present invention demonstrates a reduced food effect, being approximately equally effective when administered to a patient on an empty or full stomach.

Three batches of the 1200 mg guaifenesin–60 mg dextromethorphan HBr formulation of Example 8 were dissolved to determine the amount of dextromethorphan HBr released over time. Generally, the formulations had 1200 mg of guaifenesin and 60 mg dextromethorphan HBr and were studied over a 12 hour period. The released amount of dextromethorphan HBr was determined as a weight percent of dissolved dextromethorphan in contrast to the total weight of dextromethorphan prior to dissolution. After 1 hour about 46% to 47% of the dextromethorphan had dissolved. After 2 hours the about 59% to 60% had dissolved, after 6 hours 73% to 76% had dissolved, and after 12 hours about 86% to 89% by weight of the dextromethorphan had dissolved. Thus, the formulations of the invention reproducibly release dextromethorphan over time. See FIG. 12.

A reference sustained release formulation of guaifenesin was compared to two formulations of the present invention. Formulations B and C of FIG. 13, exhibited guaifenesin release profiles similar to the reference formulation. The reference formulation for FIG. 13 was formulation IV of Example 5. Formulation B comprised 77% guaifenesin by weight, 3.8% by weight dextromethorphan, 9.1% by weight microcrystalline cellulose, 1.9% by weight METHOCEL E10M, and 0.9% CARBOPOL® 974P. Formulation C comprised 76.5% by weight guaifenesin, 3.8% by weight dextromethorphan, 9.7% by weight microcrystalline cellulose, 1.9% by weight METHOCEL E10M, and 0.9% by weight CARBOPOL® 974P. Formulations B and C exhibited similar behavior and had a guaifenesin release profile similar to the reference formulation. Accordingly, the combination formulations of the invention did not interfere with the release of guiafenesin. In particular, after 12 hours Formulation C released a greater dose of guiafenesin than the reference formulation.

Figure 13:
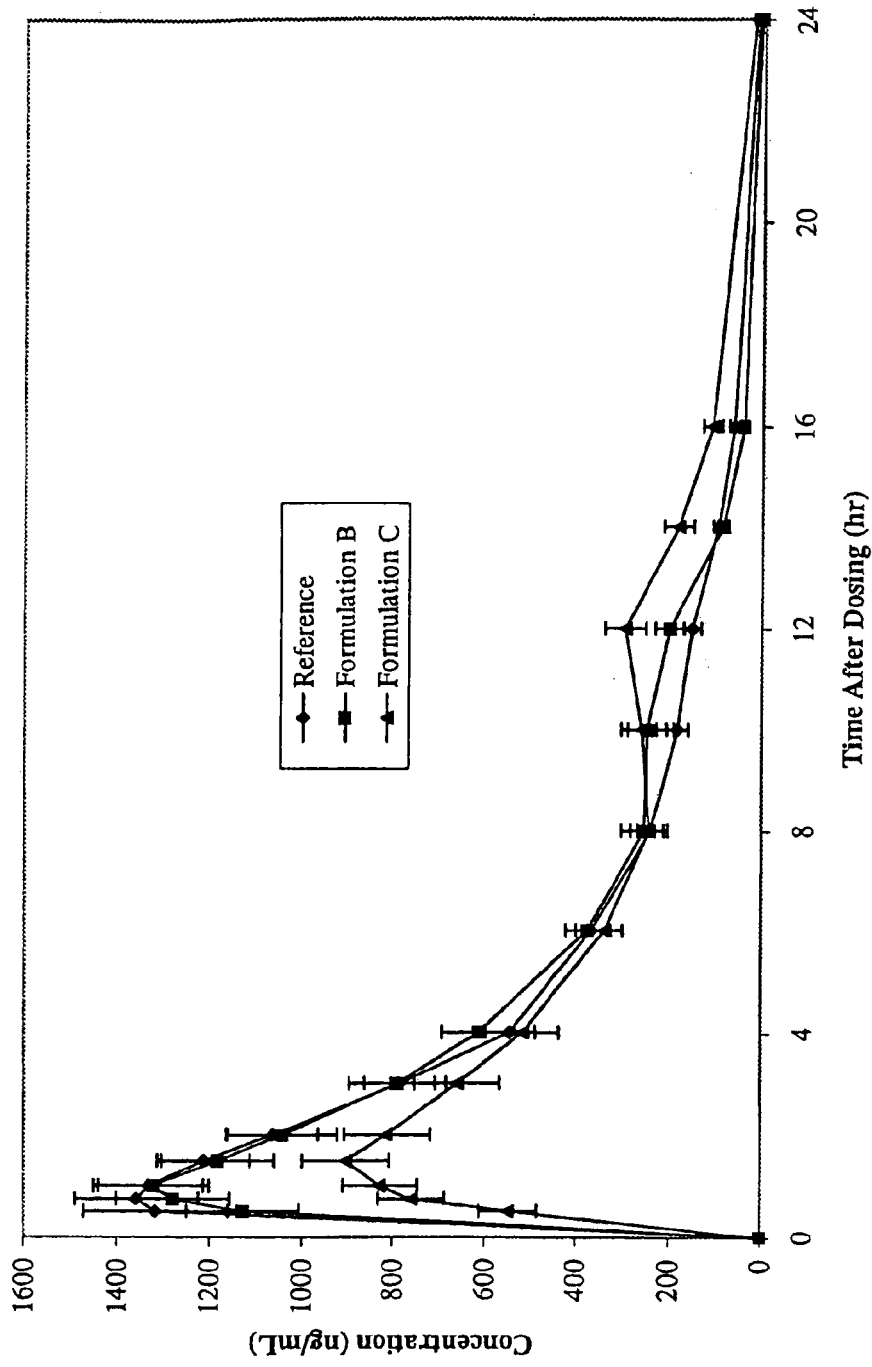
FIG. 13 is a graph demonstrating the plasma concentration of guaifenesin following the administration of 1200 mg guaifenesin and 60 mg dextromethorphan HBr to volunteers separately and in formulations of the present invention.
Figure 14:
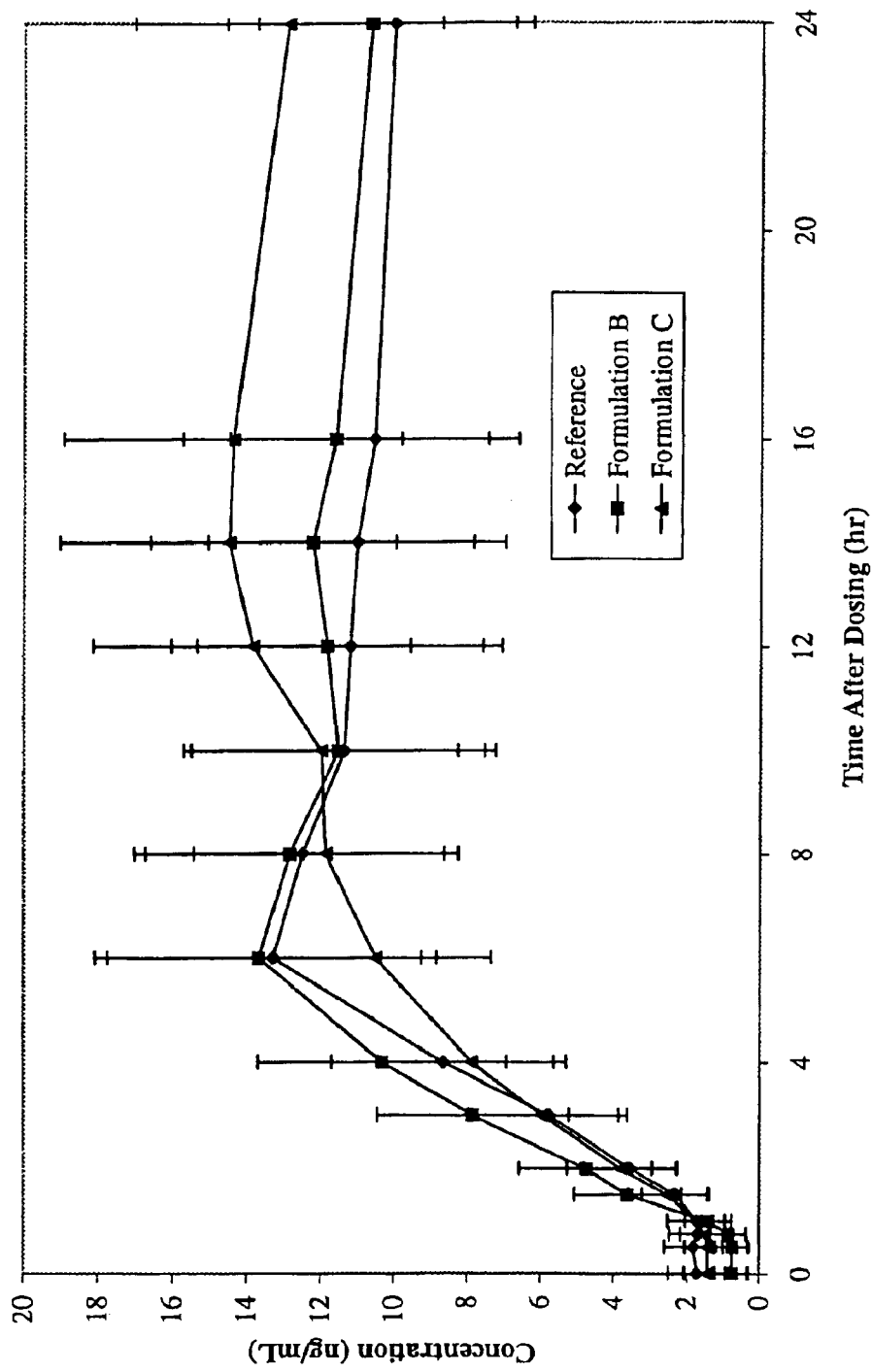
FIG. 14 is a graph demonstrating the plasma concentrations of dextromethorphan HBr following the administration of 1200 mg guaifenesin and 60 mg dextromethorphan HBr to volunteers in three different formulations.

Formulations B and C of FIG. 13 were compared against a reference consisting of an extended release formulation of dextromethorphan commercially available under the name Delsym sold by Celltech Medica. The comparison was carried out to determine the behavior of guaifenesin-dextromethorphan formulations of the invention as compared to separately administered combination formulations of dextromethorphan. Formulations B and C had longer dextromethorphan release profiles than the reference, as shown in FIG. 14. Additionally, the combined formulations of the present inventions had no detrimental effect upon the release profile of dextromethorphan.

Figure 15:
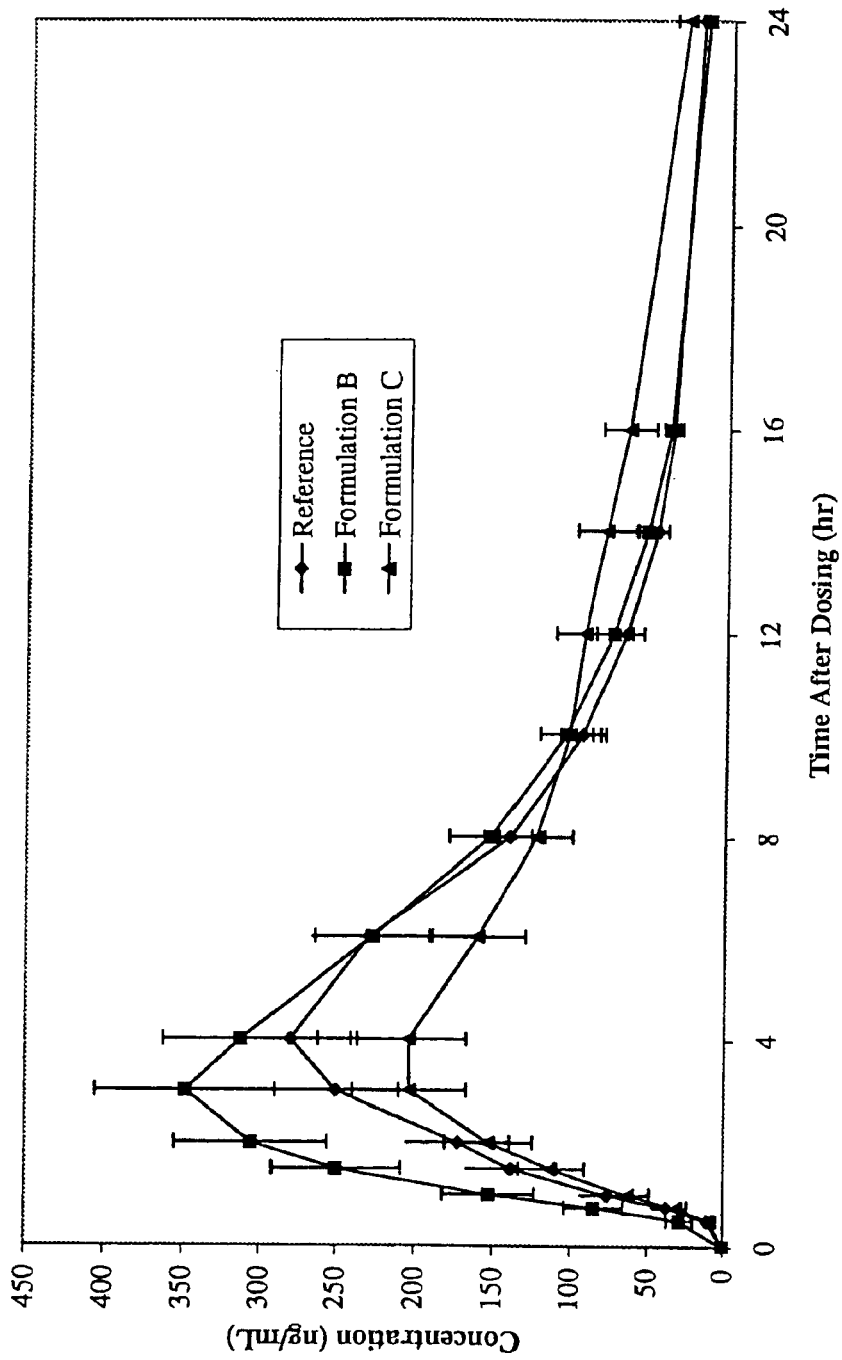
FIG. 15 is a graph demonstrating the plasma concentrations of the metabolite dextrorphan following the administration of 1200 mg guaifenesin and 60 mg dextromethorphan HBr to volunteers in three different formulations.

Another method to monitor dextromethorphan plasma concentrations is to measure the plasma concentration of the metabolite dextrorphan. The plasma concentration of dextrorphan metabolite of the reference formulation and Formulations B and C of FIG. 14 were plotted in FIG. 15. Generally, the formulations exhibited similar dextrorphan concentrations, with Formula C exhibiting the highest dextrorphan concentration after 12 hours. FIG. 15 demonstrates that the formulations of the present invention containing guaifenesin do not inhibit the release of dextromethorphan, as determined by measuring the presence of the metabolite dextrorphan.

Three batches of the 1200 mg guaifenesin–120 mg pseudoephedrine HCl formulation of Example 10 were dissolved to determine the amount of pseudoephedrine HCl released over time. Generally, the formulations had 1200 mg of guaifenesin and 120 mg pseudoephedrine HCl and were studied over a 12 hour period. The released amount of pseudoephedrine HCl was determined as a weight percent of dissolved pseudoephedrine HCl in contrast to the total weight of pseudoephedrine HCl prior to dissolution. After 1 hour about 43% to 45% of the pseudoephedrine HCl had dissolved. After 2 hours the about 58% to 60% dissolved, after 6 hours 82% to 89% had dissolved, and after 12 hours about 96% to 97% by weight of the pseudoephedrine HCl had dissolved. See FIG. 16.

Figure 17:
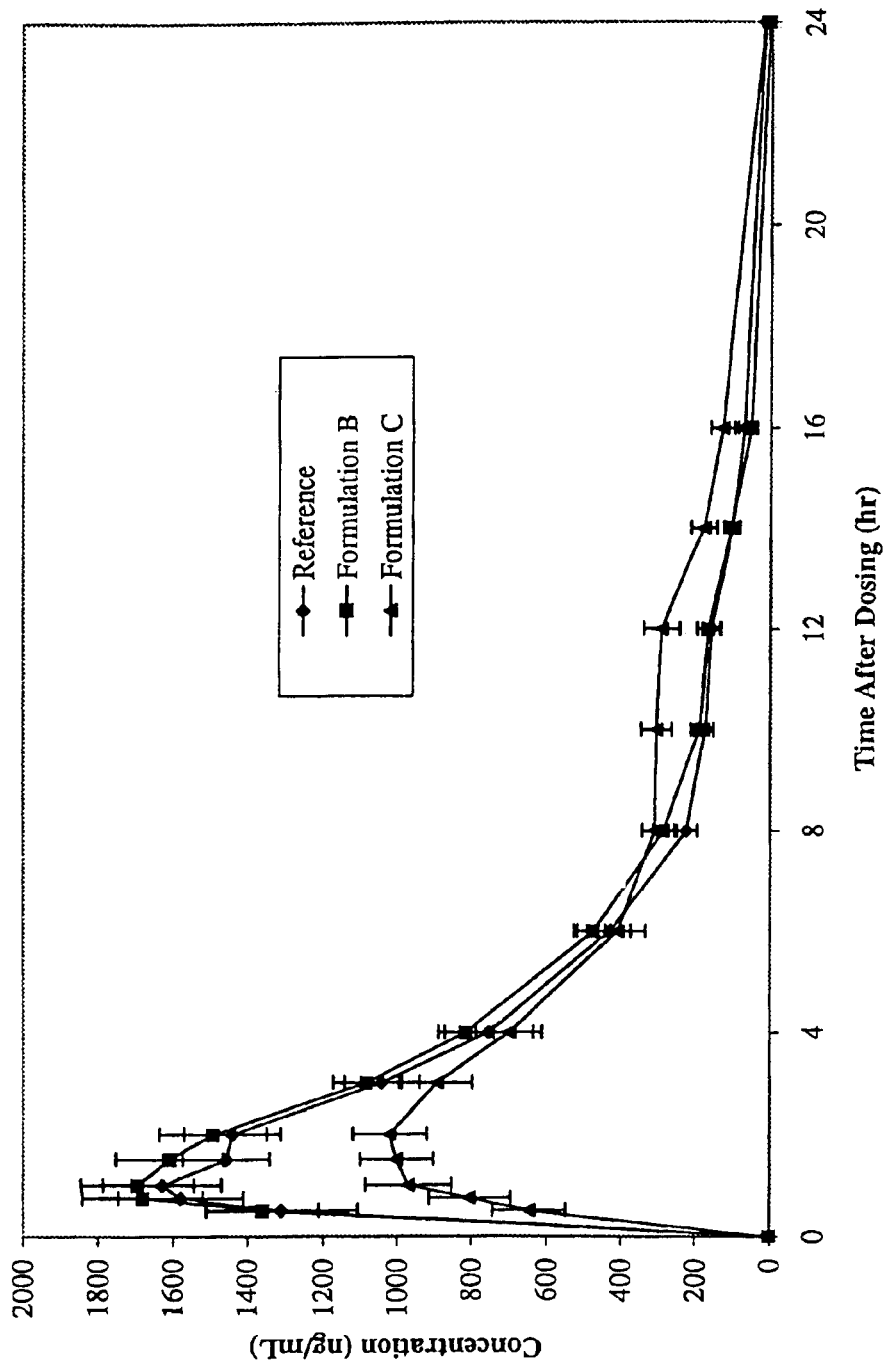
FIG. 17 is a graph demonstrating the plasma concentration of guaifenesin following the administration of 1200 mg guaifenesin and 120 mg pseudoephedrine HCl to volunteers separately and in formulations of the present invention.

Three formulations of guiafenesin, two also containing an additional ingredient, pseudoephedrine, were compared to determine whether an additional ingredient affects the release profile of guiafenesin. In FIG. 17, the reference formulation included formulation IV of Example 5 and a separate Sudafed® 12 hour formulation available from Pfizer Inc. 201 Tabor Road, Morris Plains, N.J., 07950. The reference formulation was compared to Formulation B and Formulation C of the present invention. Formulation B comprised a sustained release formulation having 86% by weight guaifenesin DC, 9.8% by weight pseudoephedrine HCl, 2.4% by weight hydroxypropyl methylcellulose, and 1.2% by weight CARBOPOL® 974P, and an immediate release formulation having 52% by weight guiafenesin DC and 39% by weight microcrystalline cellulose by weight. Formulation C comprised 77% by weight guaifenesin DC, 7.7% by weight pseudoephedrine, 9% by weight microcrystalline cellulose, 1.8% by weight METHOCEL E10M, and 0.9% by weight CARBOPOL® 974P. Formulations B and C exhibited similar behavior to separately administered formulations, thus demonstrating that formulations of the present invention did not interfere with the profile release of pseudoephedrine.

Figure 18:
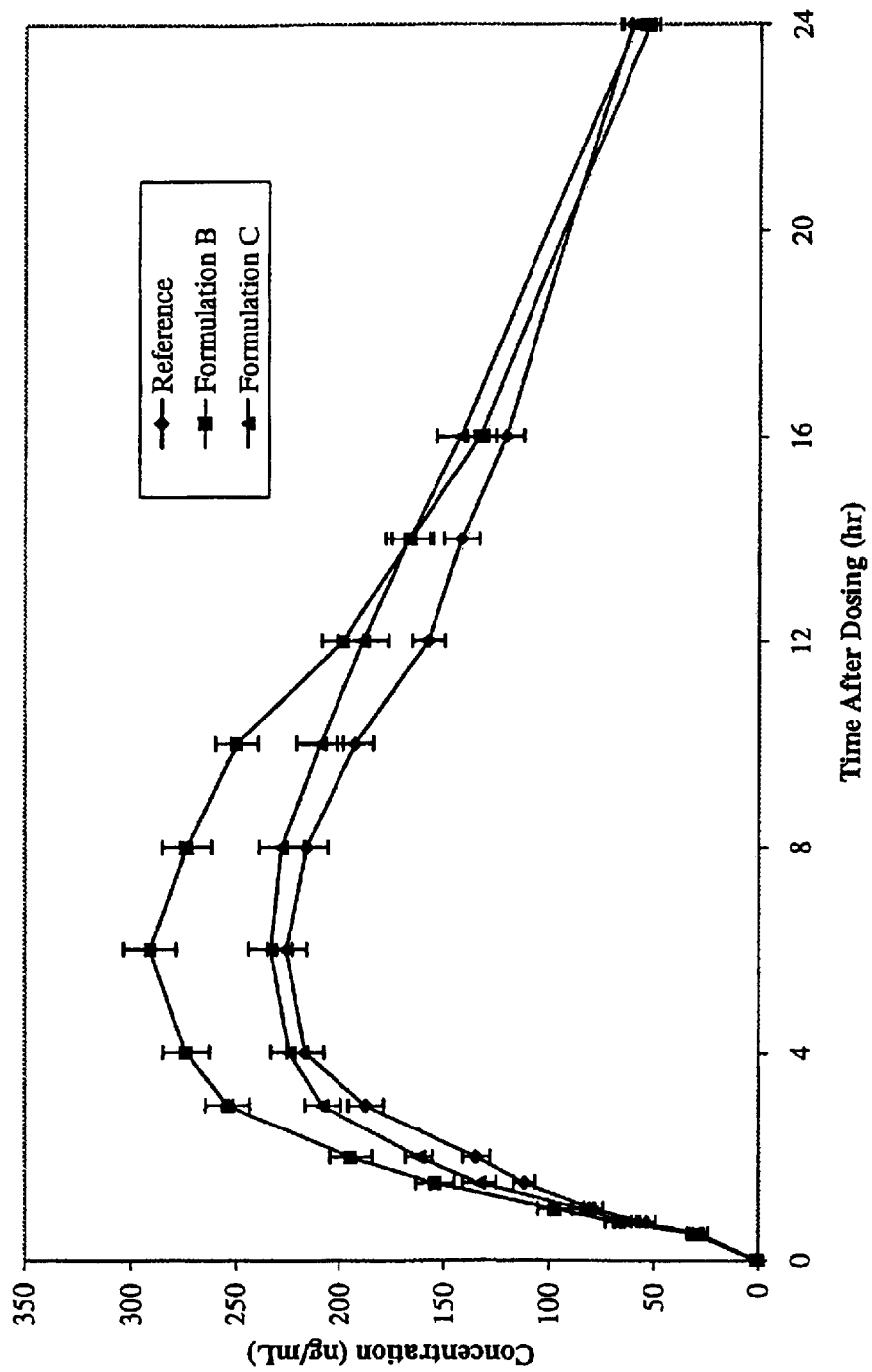
FIG. 18 is a graph demonstrating the plasma concentration of pseudoephedrine HCl following the administration of 1200 mg guaifenesin and 120 mg pseudoephedrine HCl to volunteers in three different formulations.

The plasma concentration for pseudoephedrine HCl was studied to determine whether the formulations of the present invention interfered with the release profile of pseudoephedrine. The pseudoephedrine plasma concentrations for the formulations of FIG. 17 were plotted over a 24 hour period. As illustrated in FIG. 18, Formulations B and C of FIG. 17 exhibited higher pseudoephedrine concentrations than the reference formulation. Thus, the combined formulations of the present invention release pseudoephedrine in comparable or better release profiles than formulations containing pseudoephedrine alone.

EXAMPLES

The invention is further defined by reference to the following examples describing in detail the preparation of the composition and methods of the present invention, as well as their utility. It will be apparent to those skilled in the art that many modifications, both to materials and methods, may be practiced without departing from the purpose and interest of this invention.

Example 1

A batch of sustained release guaifenesin tablets, Lot# 7LB-31FC, with the following composition was prepared:

| Components | Weight per Tablet |
|---|---|
| GUAIFENESIN DC | 1260 mg |
| METHOCEL E10M | 30 mg |
| Emerald Green Lake | 4 mg |
| Magnesium Stearate | 6.8 mg |
| Opadry Y-S-3-7413 | 13.01 mg |

Another batch of sustained release guaifenesin tablets, Lot# 7LB-32FC, with the following composition was prepared:

| Components | Weight per Tablet |
|---|---|
| GUAIFENESIN DC | 1260 mg |
| METHOCEL E10M | 30 mg |
| CARBOPOL 974P | 15 mg |
| Emerald Green Lake | 4 mg |
| Magnesium Stearate | 6.8 mg |
| Opadry Y-S-3-7413 | 13.16 mg |

Six tablets from Lot 7LB-31FC and six tablets from Lot 7LB-32FC were tested for in vitro guaifenesin release using an Acid/Base dissolution (slightly modified USP 23/NF 18 <711> Drug Release using Apparatus 2). Six dissolution vessels of a USP calibrated Hanson dissolution bath, equipped with shafts and paddles, were filled with 675 ml of 0.1N hydrochorlic acid at 37.0° C. The bath and vessels were maintained at a temperature of 37.0±0.5° C. throughout the 12 hr. dissolution test. The paddles were set to rotate at 50 RPM and slowly lowered into the vessels. One tablet of lot 7LB-31 was then dropped into each vessel.

At the one hour and two hour intervals of testing, 5 ml samples of dissolution solution were withdrawn from each vessel and filtered through a 10 micron polyethylene filter into glass HPLC vials. Immediately after the two hour samples were withdrawn, 225 ml of 0.2M sodium phosphate tribasic was added to each vessel to increase the solution pH to about 6.8. The dissolution was run for ten more hours, 2.0 ml samples being withdrawn from each vessel at the 4 hr., 8 hr., 10 hr., and 12 hr. intervals. The filtered samples from each sampling interval were then run on an HPLC to determine percent guaifenesin released from each tablet at each of the sampling intervals.

The same dissolution testing procedure was performed for lot 7LB-32 FC. The lots gave dissolution profiles shown below and depicted in FIG. 4.

Lot 7LB-31

| Vessel # | 1 HR | 2 HR | 4 HR | 8 HR | 10 HR | 12 HR |
|---|---|---|---|---|---|---|
| 1 | 26 | 38 | 55 | 77 | 84 | 88 |
| 2 | 27 | 39 | 54 | 75 | 81 | 86 |
| 3 | 22 | 37 | 50 | 73 | 78 | 85 |
| 4 | 23 | 33 | 47 | 64 | 73 | 79 |
| 5 | 25 | 36 | 52 | 75 | 81 | 86 |
| 6 | 24 | 35 | 49 | 74 | 81 | 87 |
| Average | 24.5 | 36.3 | 51.2 | 73.0 | 79.7 | 85.2 |

Lot 7LB-32FC

| Vessel # | 1 HR | 2 HR | 4 HR | 8 HR | 10HR | 12 HR |
|---|---|---|---|---|---|---|
| 1 | 25 | 36 | 42 | 54 | 59 | 64.0 |
| 2 | 24 | 35 | 42 | 55 | 61 | 66 |
| 3 | 26 | 38 | 45 | 59 | 65 | 69 |
| 4 | 24 | 35 | 42 | 54 | 60 | 65 |
| 5 | 24 | 36 | 43 | 54 | 59 | 64 |
| 6 | 23 | 34 | 38 | 50 | 55 | 59 |
| Average | 24.3 | 35.7 | 42.0 | 54.3 | 59.8 | 64.5 |

Both formulations demonstrated sustained release of guaifenesin over a 12 hour period. Lot 7LB-32FC demonstrated identical release properties to Lot 7LB-31FC in 0.1N HCl. In buffered solution, however, Lot 7LB-32FC, the lot comprising a 2:1 ratio of METHOCEL E10M to CARBOPOL 974P, demonstrated a statistically slower release than Lot 7LB-31FC, comprising METHOCEL E10M and no CARBOPOL 974P. A slower release rate in vitro translates to a slower, more controlled release with longer drug action in vivo—a favorable characteristic for pharmaceutical products containing a high concentration of an active ingredient with a short half-life.

Example 2

Figure 5:
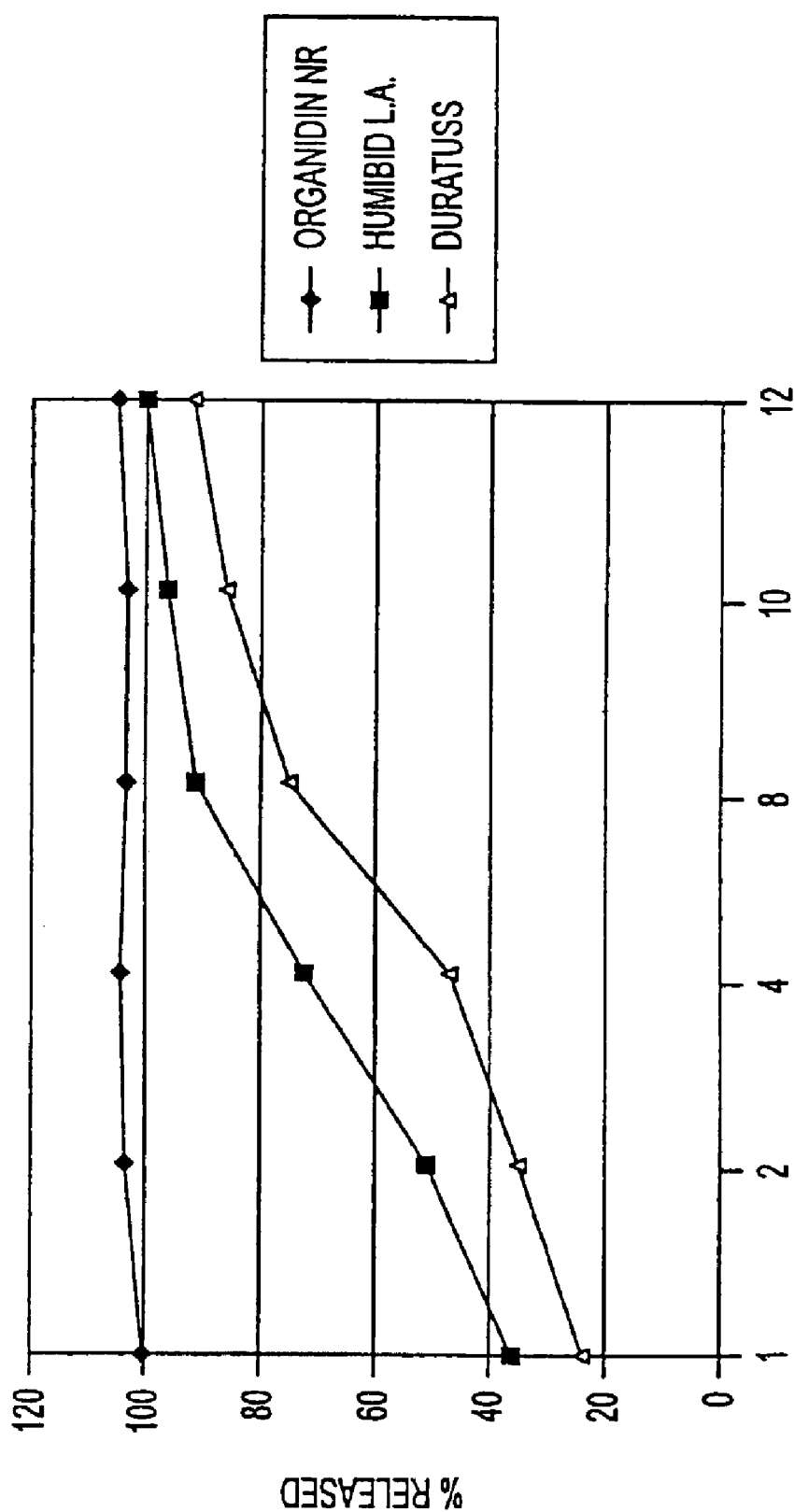
FIG. 5 is a graph demonstrating the dissolution profiles of an immediate release dosage form and two sustained release dosage forms of guaifenesin, all of which are known in the art.

A dissolution study was run to compare dissolution profiles of lots 7LB-32FC and 7LB-31FC with currently available guaifenesin dosage forms. One immediate release tablet, ORGANIDIN NR, and two sustained release tablets, HUMIBID L.A. and DURATUSS, were subjected to the same dissolution study as described for lots 7LB031FC and 7LB-32FC in Example 1 above. The following is a summary of the results which are also depicted in FIG. 5.

| | ORGANIDIN NR % guaifenesin released | HUMIBID L.A. % guaifenesin released | DURATUSS % guaifenesin released |
|---|---|---|---|
| 1 Hr | 100 | 36 | 24 |
| 2 Hr | 103 | 51 | 35 |
| 4 HR | 104 | 72 | 47 |
| 8 HR | 103 | 91 | 75 |
| 10 HR | 103 | 96 | 86 |
| 12 HR | 105 | 100 | 92 |

The immediate release ORGANIDIN released 100% of guaifenesin content within the first hour of dissolution. The two sustained release dosage forms which are currently available both demonstrated a slower release of guaifenesin. However, both the HUMIBID LA and DURATUSS released guaifenesin more rapidly than either Lot 7LB-31FC or 7LB-32FC. Both HUMIBID LA and DURATUSS would, therefore, exhibit a faster rate of release and thus a shorter lived therapeutic effect in vivo.

Example 3

The in vivo behavior of sustained release tablets of Lot 7LB-31FC and Lot 7LB-32FC from Example 1 were compared to the in vivo behavior of an immediate release formulation (ORGANIDIN NR). The open-label study involved 9 healthy volunteers averaging 38±11.01 years of age with a range of 23 years to 55 years of age. The subjects weighed 175.56±24.22 lbs. with a range of 143 to 210 lbs. One subject was female and the remainder were male. Each subject received either one 1200 mg dose of one of the two above described sustained release tablets or 400 mg every four hours for 3 doses of the immediate release formulation.

Blood samples (7 ml with sodium heparin as anticoagulant) were taken prior to dosing and at specific intervals up to 12 hours after dosing. All blood samples were chilled and centrifuged within 30 minutes of being drawn. The plasma was separated, transferred to a polypropylene tube, frozen at −20° C. or below and stored frozen until being shipped for guaifenesin analysis.

The plasma samples were analyzed by a fully validated HPLC method. The results are depicted in FIG. 6. This resulting plasma concentration v. time data was subjected to pharmacokinetic analysis using non-compartmental analysis with Winnonlin 1.5. The results of the pharmacokinetic parameters analysis are below.

| Subject | Formulation | $T_{max}$ (hr.) | $C_{max}$ (ng/ml) | $AUC_{0-12}$ (hr*ng/ml) | $T_{1/2}$ (hrs.) | $AUC_{inf}$ (hr*ng/ml) |
|---|---|---|---|---|---|---|
| 1 | 7LB-31FC | 2.00 | 827.02 | 4817.20 | 4.64 | 6339.25 |
| 2 | 7LB-31FC | 1.50 | 834.65 | 4695.89 | 2.71 | 5291.71 |
| 3 | 7LB-31FC | 1.50 | 802.44 | 4142.14 | 3.44 | 4728.33 |
| 4 | 7LB-32FC | 0.75 | 625.48 | 3034.31 | 5.78 | 5134.35 |
| 5 | 7LB-32FC | 1.00 | 1052.00 | 5872.46 | 5.99 | 8298.33 |
| 6 | 7LB-32FC | 2.00 | 1372.00 | 7924.35 | 5.53 | 9557.78 |
| 7 | ORGANIDIN NR | 0.50 | 2140.00 | 6921.94 | 0.86 | 7009.68 |
| 8 | ORGANIDIN NR | 4.25 | 18.17.00 | 6598.26 | 0.73 | 6674.65 |
| 9 | ORGANIDIN NR | 0.50 | 2831.00 | 9389.76 | 0.81 | 9570.91 |
| Mean | 7LB-31FC | 1.67 | 821.37 | 4551.74 | 3.59 | 5453.10 |
| Mean | 7LB-32FC | 1.25 | 1016.49 | 5610.37 | 5.77 | 7663.49 |
| Mean | ORGANIDIN NR | 1.75 | 2262.67 | 7636.65 | 0.80 | 7751.74 |
| Ratio (%) | 7LB-31FC/IR | 95.24 | 36.30 | 59.60 | 448.27 | 70.35 |
| Ratio (%) | 7LB-32FC/IR | 71.43 | 44.92 | 73.47 | 718.92 | 98.86 |

Subjects given the 1200 mg formulation 7LB-32FC reached maximum plasma guaifenesin concentrations of 1016 ng/mL in 1.25 hours and had an $AUC_{inf}$ of 7663 hr*ng/ml. The subjects given formulation 7LB-31FC reached maximum plasma guaifenesin concentrations of 821 ng/mL in 1.67 hours and had an $AUC_{inf}$ of 5453 hr*ng/ml. The subjects given the immediate release formulation, ORGANIDIN NR, reached maximum plasma guaifenesin concentrations of 2263 ng/ml in 1.75 hours (2 subjects peaked at 0.5 hours after the first dose and the third peaked at 0.25 hours after the second dose at 4 hours) and had an $AUC_{inf}$ of 7752 hr*ng/ml. The two controlled release formulations demonstrated sustained release in that their half-lives were longer, 5.77 hours for the 7LB-32FC and 3.59 hours for the 7LB-31 FC compared to 0.8 hours for the immediate release formulation, ORGANIDIN NR.

Both formulations 7LB-32FC (with both METHOCEL E10M and CARBOPOL 974P) and 7LB-31FC (with METHOCEL E10M only) control the release of guaifenesin from the tablet compared to the immediate release ORGANIDIN NR. Formulation 7LB-32FC, the formulation containing a 6:1 ratio of METHOCEL E10M to CARBOPOL 974P, had the longest half life at 5.77 hours with the largest $AUC_{inf}$ between the two sustained release formulation. However, both sustained release formulation has a $C_{max}$ that was less than half of the $C_{max}$ of the immediate release ORGANIDIN NR.

Example 4

Three different modified release tablet lots were prepared with the following compositions:

Sustained Release Formulation I, Non-layered Tablet

| Components | Weight per Tablet |
|---|---|
| GUAIFENESIN DC | 1260 mg |
| METHOCEL E10M | 40 mg |
| CARBOPOL 974P | 20 mg |
| Emerald Green Lake | 4 mg |
| Magnesium Stearate | 6.8 mg |

Sustained Release Formulation II, Bi-layered, 400 mg IR and 800 mg SR
IR Formulation

| Components | Weight per Tablet |
|---|---|
| GUAIFENESIN DC | 421 mg |
| Microcrystalline Cellulose (AVICEL) | 40 mg |
| Sodium Starch Glycolate (EXPLOTAB) | 60 mg |
| Magnesium Stearate | 2 mg |

SR Formulation

| Components | Weight per Tablet |
|---|---|
| GUAIFENESIN DC | 842 mg |
| METHOCEL E10M | 27 mg |
| CARBOPOL 974P | 13.5 mg |
| Emerald Green Lake | 3 mg |
| Magnesium Stearate | 4.5 mg |

Sustained Release Formulation III, Bi-layered, 600 mg IR and 600 mg SR

IR Formulation

| Components | Weight per Tablet |
|---|---|
| GUAIFENESIN DC | 630.8 mg |
| Microcrystalline Cellulose (AVICEL) | 353 mg |
| Sodium Starch Glycolate (EXPLOTAB) | 90.1 mg |
| Magnesium Stearate | 3 mg |

SR Formulation

| Components | Weight per Tablet |
|---|---|
| GUAIFENESIN DC | 630.8 mg |
| METHOCEL E10M | 40 mg |
| CARBOPOL 974P | 20 mg |
| Emerald Green Lake | 4 mg |
| Magnesium Stearate | 6.8 mg |

The in vivo behavior of each of the three sustained release tablets and an immediate release formulation (ORGANIDIN NR) were compared. The open-label study involved 15 healthy volunteers averaging 31.67±11.89 years of age with a range of 20 years to 51 years of age. The subjects weighed 162.00±25.05 lbs. with a range of 123 to 212 lbs. All 15 subjects were administered 400 mg of the immediate release formulation every 4 hours for a total of 12 hours in on one day. On another day, 5 subjects were administered Sustained Formulation I, another 5 subjects were administered Sustained Formulation II, and yet another 5 subjects were administered Sustained Formulation III.

Blood samples (7 ml with sodium heparin as anticoagulant) were taken prior to dosing and at specific intervals up to 12 hours after dosing. All blood samples were chilled and centrifuged within 30 minutes of being drawn. The plasma was separated, transferred to a polypropylene tube, frozen at −20° C. or below and stored frozen until being shipped for guaifenesin analysis.

Figure 7:
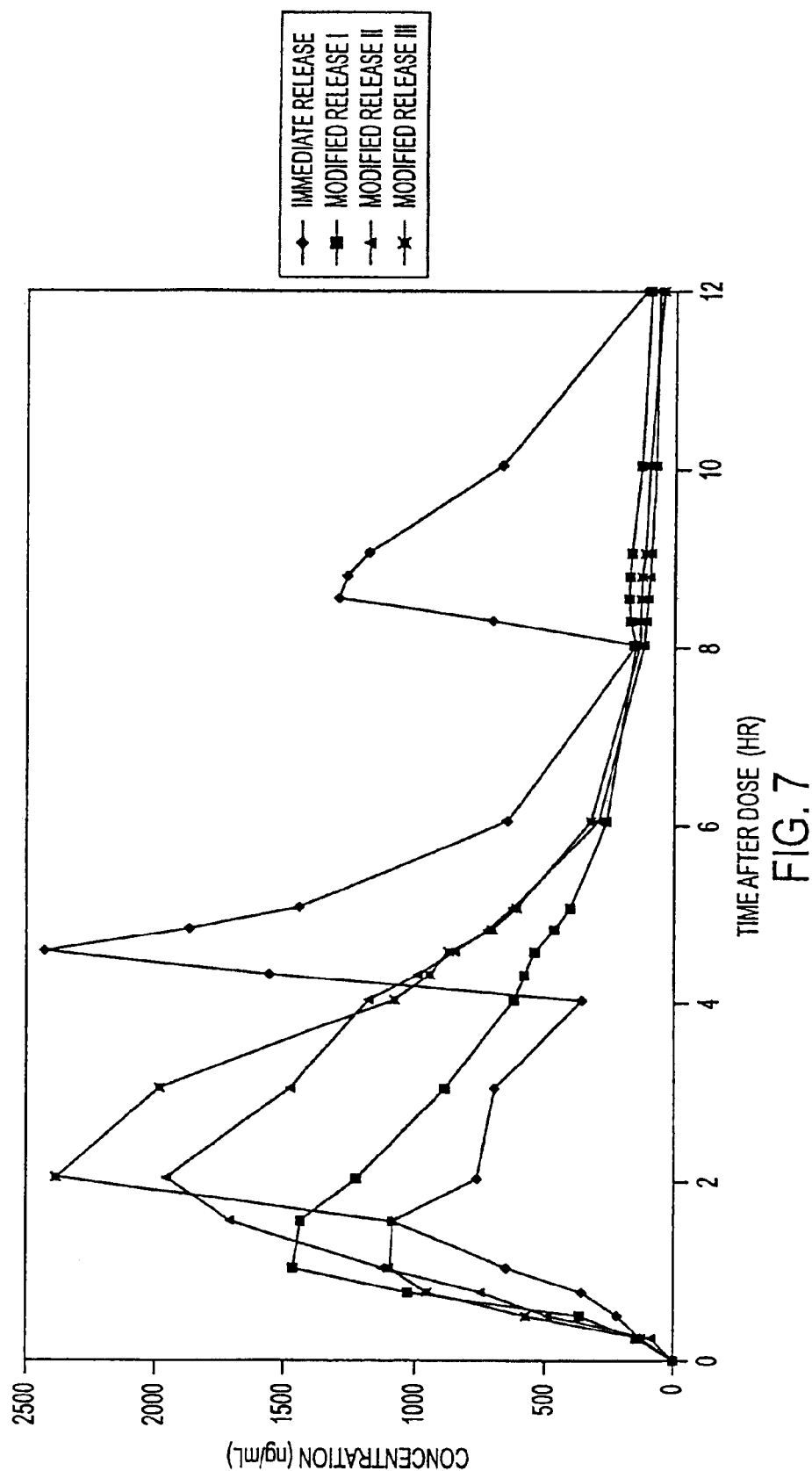
FIG. 7 is a graph demonstrating the plasma concentration of guaifenesin over time in healthy human volunteers from an immediate release tablet lot which is known in the art, a non-layered modified release tablet lot of the present invention, and two bi-layered modified release tablet lots of the present invention (one comprising 600 mg of immediate release formulation and 600 mg of sustained release formulation and the other one comprising 400 mg of immediate release formulation and 800 mg of sustained release formulation).

The plasma samples were analyzed by a fully validated HPLC method. The results are depicted in FIG. 7. This resulting plasma concentration v. time data was subjected to pharmacokinetic analysis using non-compartmental analysis with Winnonlin 1.5. The results of the pharmacokinetic parameters analysis are below.

| | Formulation | $T_{max}$ (hr.) | $C_{max}$ (ng/ml) | $AUC_{0-12}$ (hr*ng/ml) | $T_{1/2}$ (hrs.) | $AUC_{inf}$ (hr*ng/ml) |
|---|---|---|---|---|---|---|
| Mean | ORGANIDIN NR | 0.90 | 2609.40 | 8768.40 | 1.28 | 9082.78 |
| Mean | SR I | 2.30 | 1631.40 | 5549.30 | 2.88 | 6044.93 |
| Mean | SR II | 2.30 | 2415.40 | 7304.38 | 1.48 | 7509.78 |
| Mean | SR III | 1.95 | 2938.00 | 8904.62 | 2.05 | 9161.03 |

Sustained Formulations II and III exhibited a $C_{max}$ more comparable to the immediate release formulation and an increased $AUC_{inf}$ from that of the non-layered Sustained Formulation I. However, the half-lives of both Sustained Formulation II and III were reduced from the half-life of Sustained Formulation I. Although these bi-layer tablets showed an improved serum concentration of guaifenesin and an increased overall concentration with time, their half-life was compromised.

Example 5

A dissolution study was run to compare dissolution profiles of Formulation I, Formulation II and Formulation III prepared as defined in Example 4 above, and Formulation IV, a bi-layer tablet lot with 200 mg IR and 1000 mg SR prepared with the following composition:

IR Formulation

| Components | Weight per Tablet |
|---|---|
| GUAIFENESIN DC | 211 mg |
| Microcrystalline Cellulose (AVICEL) | 118 mg |
| Sodium Starch Glycolate (EXPLOTAB) | 30 mg |
| Magnesium Stearate | 1 mg |

SR Formulation

| Components | Weight per Tablet |
|---|---|
| GUAIFENESIN DC | 1053 mg |
| METHOCEL E10M | 25 mg |
| CARBOPOL 974P | 12.5 mg |
| Emerald Green Lake | 3.3 mg |
| Magnesium Stearate | 5.7 mg |

Figure 8:
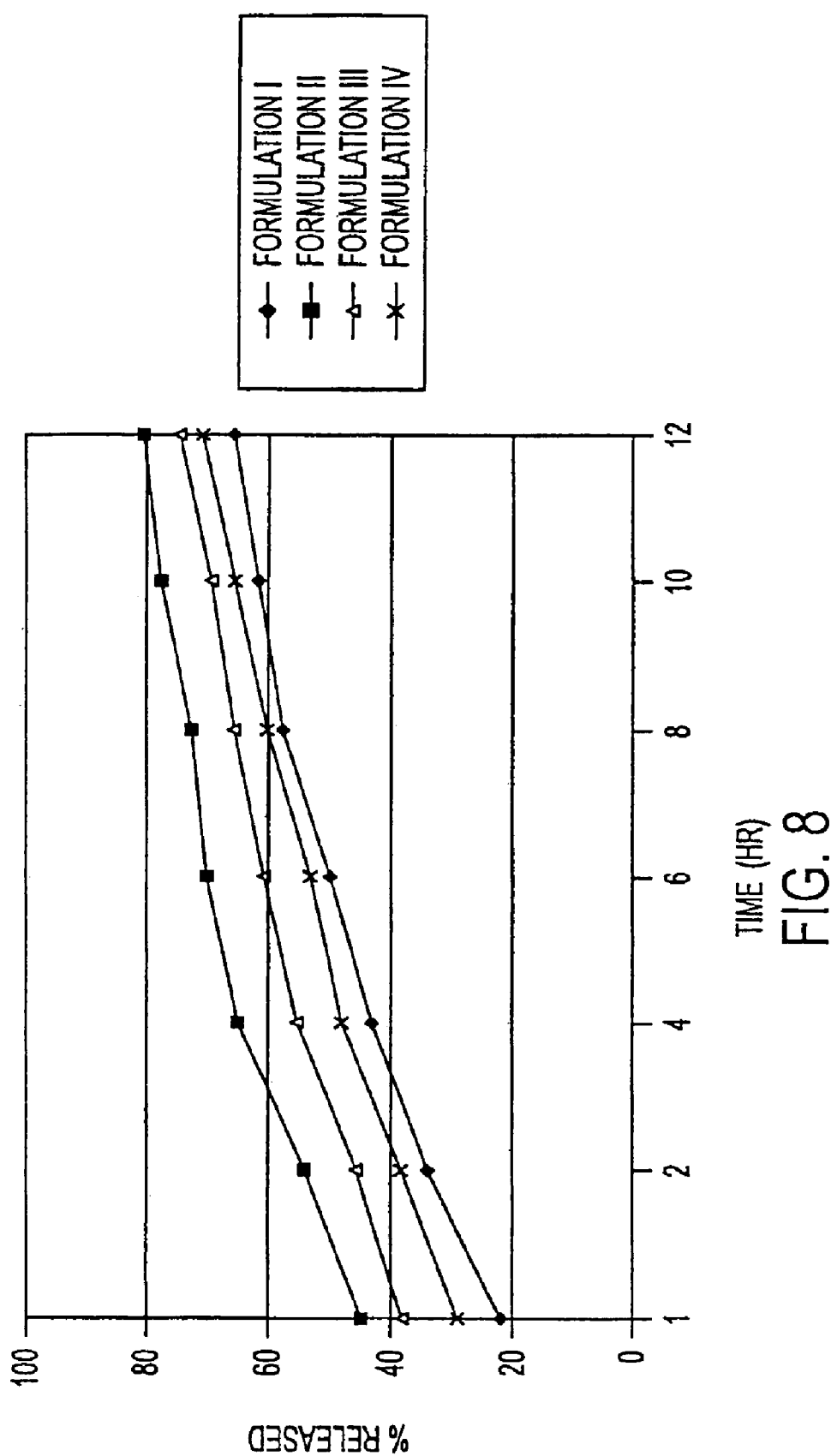
FIG. 8 is a graph demonstrating the dissolution profiles of four sustained release tablets of the present invention: one tablet is non-layered, comprising 1200 mg of sustained release formulation; another tablet is bi-layered, comprising 600 mg of sustained release formulation and 600 mg of immediate release formulation; another tablet is bi-layered, comprising 800 mg of sustained release formulation and 400 mg of immediate release formulation; and yet another tablet is bi-layered comprising 1000 mg of sustained release formulation and 200 mg of immediate release formulation.

The following is a summary of the results which are also depicted in FIG. 8.

| | Formulation I % released | Formulation II % released | Formulation III % released | Formulation IV % released |
|---|---|---|---|---|
| 1 hr | 22 | 45 | 38 | 29 |
| 2 hr | 34 | 54 | 46 | 38 |
| 4 hr | 43 | 65 | 56 | 48 |
| 6 hr | 50 | 70 | 61 | 53 |
| 8 hr | 58 | 73 | 66 | 60 |
| 10 hr | 62 | 78 | 70 | 66 |
| 12 hr | 66 | 81 | 75 | 71 |

Formulation I, the non bi-layered tablet, demonstrated the slowest release of guaifenesin. Formulation II and Formulation III had the fastest rates of release and would, therefore, exhibit a faster rate of release and thus a shorter lived therapeutic effect in vivo. Formulation IV has a rate of release which was faster than Formulation I, comprising no immediate release blend, but slower than Formulation II and Formulation III, both comprising more immediate release blend than Formulation IV.

Example 6

The in vivo behavior of Formulation IV bi-layered tablets, prepared as described above in Example 5, was compared to an immediate release formulation (ORGANIDIN NR). The open-label, multiple dose, randomized, 2-way crossover study involved 26 healthy volunteers averaging 31.31±9.81 years of age with a range of 19 years to 50 years of age. The subjects weighed 166.77±29.83 lbs. The subjects were placed into one of two treatment groups. Group 1 received Formulation IV tablet with 240 ml of water after an overnight fast every 12 hours for 5 days and a single dose on day 6. Group 2 received 400 mg of ORGANIDIN NR (2×200 mg tablets) with 240 ml of water every 4 hours for 5 days and one 400 mg dose every four hours for a total of 3 doses on day 6.

Blood samples (5 ml with sodium heparin as anticoagulant) were taken prior to dosing on days 1, 4, 5, and 6. On Day 1, additional blood samples (5 ml with sodium heparin as anticoagulant) were also obtained at 0.5, 0.75, 1, 1.5, 2, 3, 4, 4.5, 4.75, 5, 5.5, 6, 7, 8, 8.5, 8.75, 9, 9.5, 10, 11, and 12 hours after the initial dose. On Day 6, additional blood samples (5 ml with sodium heparin as anticoagulant) were also obtained at 0.5, 0.75, 1, 1.5, 2, 3, 4, 4.5, 4.75, 5, 5.5, 6, 7, 8, 8.5, 8.75, 9, 9.5, 10, 11, 12, 14, 16, and 24 hours after the initial dose. Plasma was separated and the plasma frozen until analyzed for guaifenesin content. The resulting plasma concentration data was subjected to pharmacokinetic and statistical analysis in order to determine if the sustained release tablets performed as controlled release tablets at steady state.

The results of the pharmacokinetic parameters analysis are below.

Averaged Testing—11 Twelve-Hour Intervals

| Formulation | $T_{max}$ (hr.) | $C_{max}$ (ng/ml) | $AU_{0-12}$ (hr*ng/ml) | $T_{1/2}$ (hrs.) | $AUC_{inf}$ (hr*ng/ml) |
|---|---|---|---|---|---|
| Mean ORGANIDIN NR | 1.69 | 2463.20 | 8381.93 | 0.78 | 8528.51 |
| Mean Bi-layered Tablet | 1.05 | 2111.38 | 7875.68 | 3.31 | 8686.08 |

Figure 9:
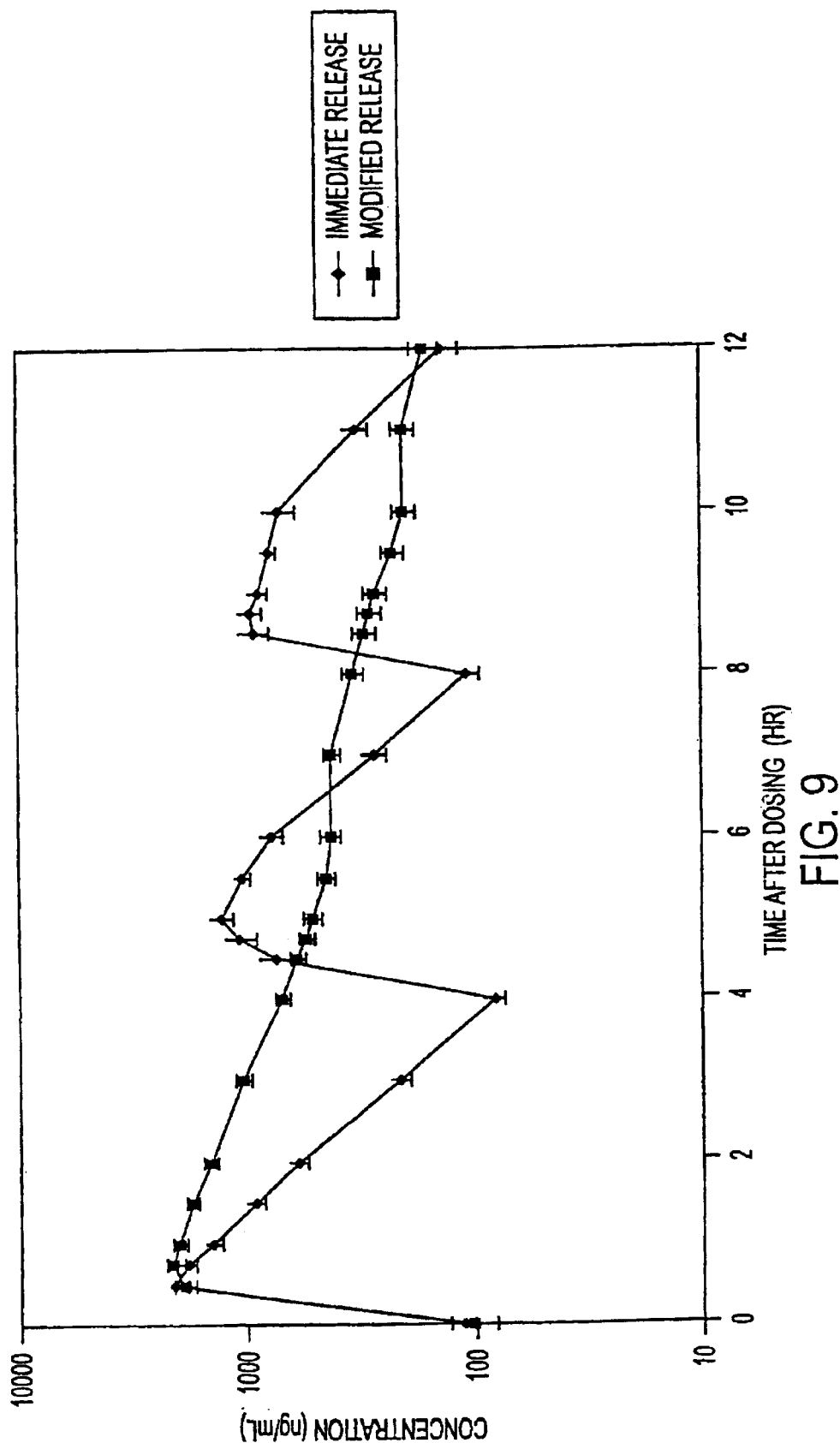
FIG. 9 is a graph demonstrating the plasma concentration of guaifenesin over an averaged 12 hour interval (taken from 11 twelve hour intervals over 5.5 days) in healthy human volunteers from an immediate release tablet lot known in the art and a bi-layered modified release tablet lot of the present invention.

The results of the testing are depicted in FIG. 9.

Steady State Testing

| Formulation | $T_{max}$ (hr.) | $C_{max}$ (ng/ml) | $AUC_{0-12}$ (hr*ng/ml) | $T_{1/2}$ (hrs.) | $AUC_{inf}$ (hr*ng/ml) |
|---|---|---|---|---|---|
| Mean ORGANIDIN NR | 2.03 | 2278.20 | 7751.23 | 0.88 | 7962.14 |
| Mean Bi-layered Tablet | 0.86 | 2349.6 | 8202.47 | 3.61 | 9259.24 |

Figure 10:
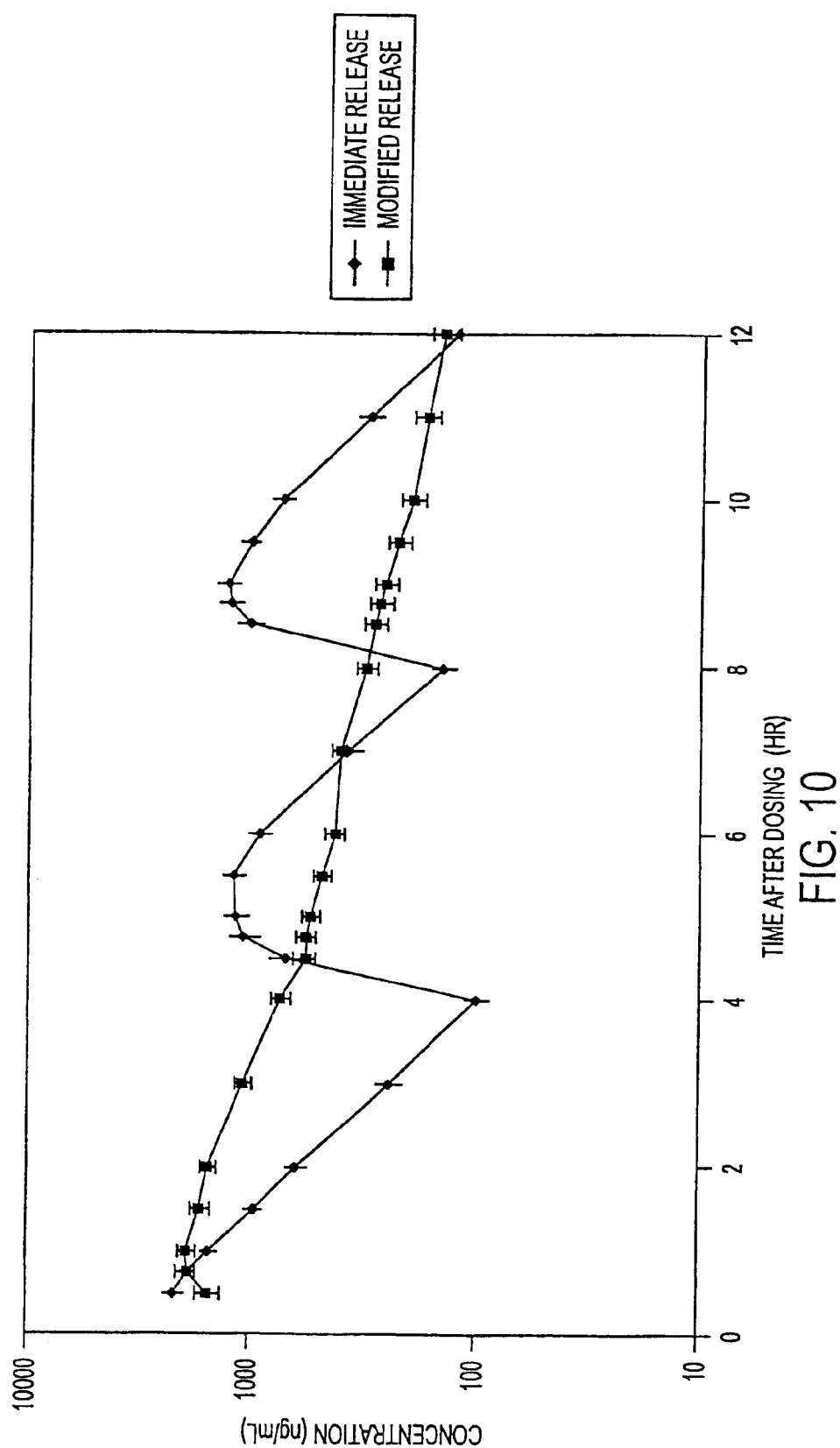
FIG. 10 is a graph demonstrating the plasma concentration of guaifenesin over time (the last twelve hour interval of the 11 twelve hour intervals described above) in healthy human volunteers from an immediate release tablet lot known in the art and a bi-layered modified release tablet lot of the present invention.

The results of the testing are depicted in FIG. 10.

The 200/1000 mg bi-layered tablet exhibited a $C_{max}$ and a $AUC_{inf}$ equivalent to that of the immediate release blend, a short $T_{max}$ and an extended half-life. Thus, a bi-layered tablet with 200 mg guaifenesin in the immediate release formulation and 1000 mg of guaifenesin in the sustained release formulation results in a tablet which delivers a high serum concentration in a short period of time, yet maintains an effective concentration of guaifenesin in the blood stream for a full twelve hours.

Example 7

A study was performed to examine the relative bioavailability of two different dosage strengths of modified release guaifenesin formulations of the present invention as well as the effect of food on the relative bioavailability of a guaifenesin formulation of the present invention in normal, healthy male and/or female volunteers. Two batches of guaifenesin bi-layer tablets, one 600 mg and one 1200 mg, were prepared according to the following composition.

600 mg Tablet

IR Formulation

| Components | Weight per 200,000 Tablets |
|---|---|
| GUAIFENESIN DC | 21.05 kg |
| Microcrystalline Cellulose (AVICEL PH102) | 11.75 kg |
| Sodium Starch Glycolate (EXPLOTAB) | 3.00 kg |
| Magnesium Stearate | 0.10 kg |

SR Formulation

| Components | Weight per 200,000 Tablets |
|---|---|
| GUAIFENESIN DC | 105.27 kg |
| Hydroxypropyl Methyl Cellulose (METHOCEL E10M) | 2.50 kg |
| Carbomer (CARBOPOL 974P) | 1.25 kg |
| FD&C Blue #1 Aluminum Lake Dye | 0.33 kg |
| Magnesium Stearate | 0.57 kg |

1200 mg Tablet

IR Formulation

| Components | Weight per 100,000 Tablet |
|---|---|
| GUAIFENESIN DC | 21.05 kg |
| Microcrystalline Cellulose (AVICEL PH102) | 11.75 kg |
| Sodium Starch Glycolate (EXPLOTAB) | 3.00 kg |
| Magnesium Stearate | 0.10 kg |

SR Formulation

| Components | Weight per 100,000 Tablets |
|---|---|
| GUAIFENESIN DC | 105.27 kg |
| Hydroxypropyl Methyl Cellulose (METHOCEL E10M) | 2.50 kg |
| Carbomer (CARBOPOL 974P) | 1.25 kg |
| FD&C Blue #1 Aluminum Lake Dye | 0.33 kg |
| Magnesium Stearate | 0.57 kg |

Note: the 600 mg and 1200 mg tablets were similarly prepared, the only difference between the dosage forms being that the 1200 mg tablet contained about twice as much of each ingredient as the 600 mg tablet.

The in vivo behaviors of a 600 mg tablet administered to volunteers in the fasting state (about 10 hours pre-dose until about 4 hours after dosing), the 1200 mg tablet administered to volunteers in the fasting state (about 10 hours pre-dose until about 4 hours after dosing), and the 1200 mg tablet administered to volunteers after a high fat meal (consumed within 30 minutes of dosing) were compared. The open-label study involved 27 healthy volunteers between the ages of 18 and 55. The subjects weighed within 15% of their Ideal Body Weight as defined by the 1983 Metropolitan Life chart. The 27 volunteers were divided into 3 treatment groups, 9 receiving the 600 mg tablet, 9 receiving the 1200 mg tablet while fasting, and 9 receiving a 1200 mg tablet after consuming a high fat meal for Period 1 of the trial. After completion of Period 1, the volunteers were crossed-over for Period 2 (e.g. so that the 9 volunteers who had been receiving the 600 mg tablet in Period 1 received the 1200 mg tablet while fasting in Period 2). After completion of Period 2, the volunteers were crossed-over again into their 3rd and final treatment group (i.e. the 9 volunteers who received the 1200 mg tablet while fasting in Period 2 and the 600 mg tablet while fasting in Period 1 received the 1200 mg tablet after consumption of a high fat meal in Period 3). Each volunteer was administered one dose of the appropriate tablet and then monitored over a 16 hour period.

Blood samples (7 ml with sodium heparin as anticoagulant) were taken about one hour prior to dosing and at specific intervals up to 16 hours after dosing (at 0.25, 0.5, 0.75, 1, 1.5, 2, 3, 4, 6, 8, 10, 12, 14, and 16 hours). All blood samples were chilled and centrifuged within 30 minutes of being drawn. The plasma was separated, transferred to a polypropylene tube, frozen at −20° C. or below and stored frozen until being shipped for guaifenesin analysis. The volunteers were then given at least a seven day washout period (where no guaifenesin was administered to them under the study) prior to being crossed-over to the next treatment group.

Figure 11:
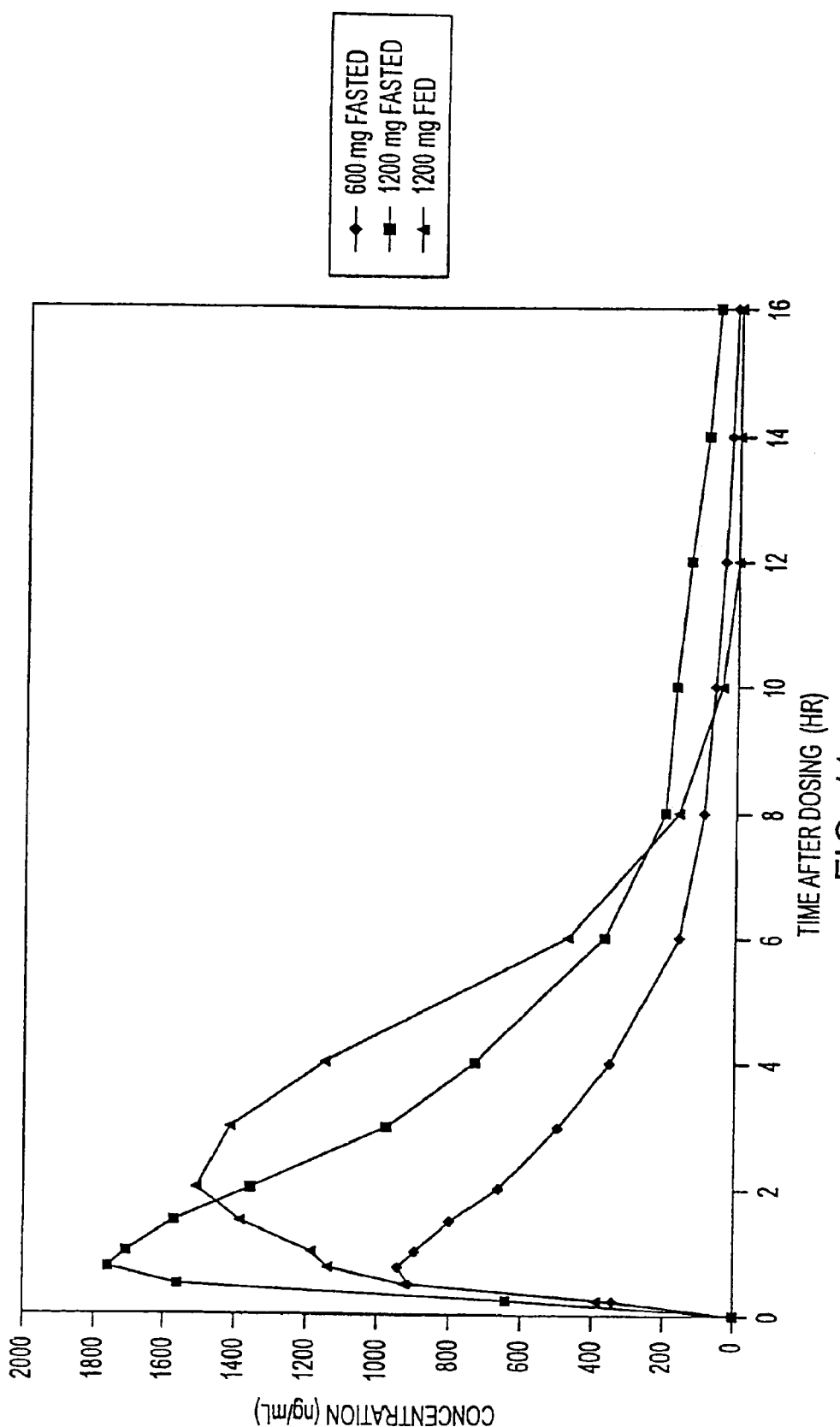
FIG. 11 is a graph demonstrating the averaged plasma concentration of guaifenesin over a 16 hour period in 27 healthy human volunteers from 600 mg bi-layered modified release tablets of the present invention administered to fasting volunteers, 1200 mg bi-layered modified release tablets of the present invention administered to fasting volunteers, and 1200 mg bi-layered modified release tablets of the present invention administered to volunteers who had been fed a high fat meal.

The plasma samples were analyzed by a fully validated HPLC method. The results are depicted in FIG. 11. This resulting plasma concentration v. time data was subjected to pharmacokinetic analysis using non-compartmental analysis with Winnonlin 1.5. The results of the pharmacokinetic parameters analysis are below.

| Formulation | $T_{max}$ (hr.) | $C_{max}$ (ng/ml) | $AUC_{0-12}$ (hr*ng/ml) | $T_{1/2}$ (hrs.) | $AUC_{inf}$ (hr*ng/ml) |
|---|---|---|---|---|---|
| Mean 600 mg Fasted | 0.81 | 1074.26 | 3623.03 | 2.33 | 3676.23 |
| Mean 1200 mg Fasted | 0.94 | 1948.62 | 7483.20 | 3.33 | 7912.61 |
| Mean 1200 mg Fed | 2.18 | 1988.08 | 7424.20 | 0.91 | 7425.29 |

The 600 mg tablet demonstrated a serum profile approximately directly proportional to the serum profile of the 1200 mg tablet. The $C_{max}$ of the 600 mg tablet was about 55% that of the 1200 mg tablet. The $AUC_{0-12}$ of the 600 mg tablet was about 48% that of the 1200 mg tablet and the $AUC_{inf}$ of the 600 mg tablet was about 46% that of the 1200 mg. improved serum concentration of guaifenesin and an increased overall concentration with time, their half-life was compromised.

The 1200 mg tablet demonstrated that the bi-layer tablets of this invention greatly reduce the food effect in bioavailability and serum concentration of guaifenesin. The $C_{max}$ of the 1200 mg tablet administered after a high fat meal (fed tablet) was about 102% of the $C_{max}$ of the 1200 mg tablet administered after fasting (fasted tablet). The $AUC_{0-12}$ of the 1200 mg fed tablet was about 99% that of the fasted tablet and the $AUC_{inf}$ of the 1200 mg fed tablet was about 94% that of the fasted tablet.

Example 8

Two batches of guaifenesin/dextromethorphan HBr bi-layer tablets, one 600 mg and one 1200 mg, were prepared according to the following composition. In the 30 mg dextromethorphan tablet 7.5 mg was within the immediate release layer and 22.5 mg within the modified release layer.

600 mg Guaifenesin/30 mg Dextromethorphan Tablet

Sustained Release (SR) Formulation

| Components | Weight per 200,000 tablets (kg) |
|---|---|
| Guaifenesin, USP | 101.00 |
| Dextromethorphan HBr | 4.50 |
| CARBOPOL 974P, NF | 1.50 |
| Microcrystalline Cellulose (METHOCEL E10M) | 5.00 |
| D&C YELLOW #10 Aluminum Lake (14–18%) | 0.04 |
| Magnesium Stearate | 1.00 |

Immediate Release (IR) Formulation

| Components | Weight per 480,000 tablets (kg) |
|---|---|
| Guaifenesin, USP | 45.60 |
| Dextromethorphan HBr | 3.60 |
| Sodium Starch Glycolate, NF (Explotab) | 3.60 |
| Microcrystalline Cellulose (AVICEL PH102) | 40.32 |
| METHOCEL E10M, USP | 2.40 |
| Magnesium Stearate, NF | 0.48 |

1200 mg Guaifenesin/60 mg Dextromethorphan HBr Tablet

SR Layer Formulation

| Components | Weight per 100,000 tablets (kg) |
|---|---|
| Guaifenesin | 101.00 |
| Dextromethorphan HBr | 4.50 |
| Microcrystalline Cellulose (METHOCEL E10M) | 5.00 |
| CARBOPOL 974P, NF | 1.50 |
| FD&C Blue No. 1 Aluminum Lake (11–13%) | 0.04 |
| Magnesium Stearate | 1.0 |

IR Layer Formulation

| Components | Weight per 240,000 tablets (kg) |
|---|---|
| Guaifenesin | 45.60 |
| Dextromethorphan HBr | 3.60 |
| Sodium Starch Glycolate, NF (Explotab) | 3.60 |
| Microcrystalline Cellulose (AVICEL PH102) | 40.32 |
| METHOCEL E10M, USP | 2.40 |
| Magnesium Stearate, NF | 0.48 |

Figure 12:
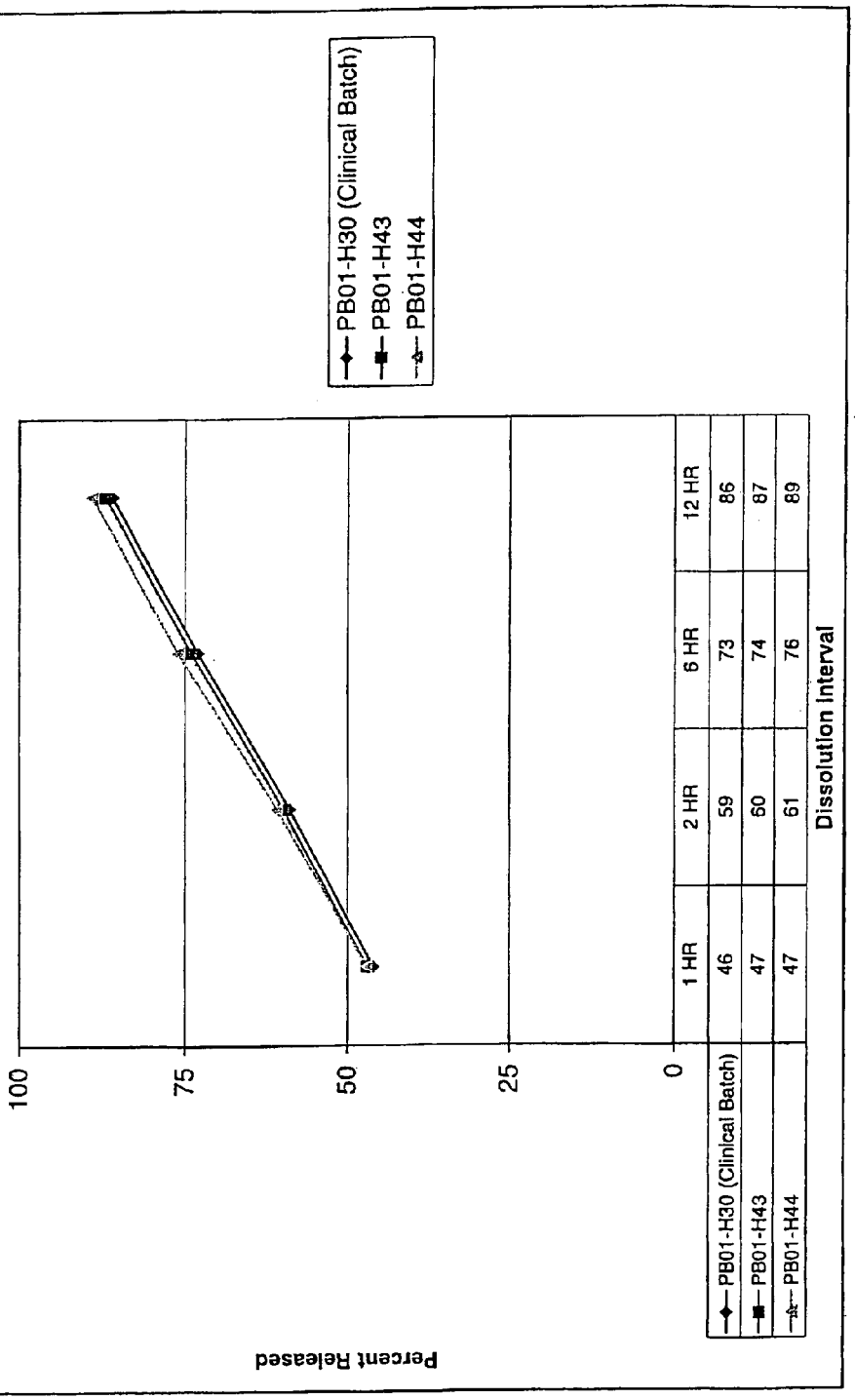
FIG. 12 is a graph demonstrating the dissolution profile of dextromethorphan HBr as measured by three different batches of a 1200 mg guaifenesin–60 mg dextromethorphan tablet over a 12 hour period as measured by the weight percentage of dextromethorphan HBr dissolved over time.

The following is a summary of the dextromethorphan HBr Dissolution Rate of the 1200 mg guaifenesin–60 mg dex tromethorphan tablet results which are also depicted in FIG. 12.

|       | Formulation I % released | Formulation II % released | Formulation III % released |
|-------|--------------------------|---------------------------|----------------------------|
| 1 hr  | 46                       | 47                        | 47                         |
| 2 hr  | 59                       | 60                        | 61                         |
| 6 hr  | 73                       | 74                        | 76                         |
| 12 hr | 86                       | 87                        | 89                         |

The in vivo behavior of the 1200 mg guaifenesin and 60 mg tablet was studied by measuring the plasma concentration of guaifenesin, dextromethorphan HBr, and the metabolite dextrorphan. FIGS. 13–15 illustrate the plasma concentration for each drug or metabolite in two formulations, Formulation B and Formulation C, during a 24 hour period. Immediately after administration the plasma concentration of guaifenesin peaks in about an hour, followed by a gradual plasma concentration decrease over 24 hours. Immediately after administration, guaifenesin plasma concentration never decreased to less than 200 ng/ml over 12 hours. Thereafter, guaifenesin plasma concentration gradually decreased over the next 12 hours. Plasma concentration of dextromethorphan HBr peaks at about 6 hours at about 12 ng/ml and the concentration is maintained for the following 19 hours.

Example 9

A study was performed to examine the relative bioavailability of a sustained release guaifenesin with dextromethorphan formulation of the present invention with normal, healthy male and/or female volunteers. A batch of guaifenesin and dextromethorphan bi-layer tablet, 1200 mg, was prepared according to the composition described above for Example 8.

The in vivo behaviors of the 1200 mg tablet administered to volunteers in the fasting state (about 10 hours pre-dose until about 4 hours after dosing) was determined. The open-label study involved 29 healthy volunteers between the ages of 18 and 55. The subjects weighed within 15% of their Ideal Body Weight as defined by the 1983 Metropolitan Life chart. The 29 volunteers were divided into two treatment groups half receiving the 1200 mg tablet while fasting for Period 1 of the trial. Each volunteer was administered one dose of the appropriate tablet and then monitored over a 16 hour period.

Blood samples (7 ml with sodium heparin as anticoagulant) were taken about one hour prior to dosing and at specific intervals up to 16 hours after dosing (at 0.25, 0.5, 0.75, 1, 1.5, 2, 3, 4, 6, 8, 10, 12, 14, and 16 hours). All blood samples were chilled and centrifuged within 30 minutes of being drawn. The plasma was separated, transferred to a polypropylene tube, frozen at −20° C. or below and stored frozen until being shipped for guaifenesin and dextromethorphan analysis.

The plasma samples were analyzed by a fully validated HPLC method by PPD Development (3230 Deming Way Suite 190, Middleton, Wis. 53562). The resulting plasma concentration v. time data was subjected to pharmacokinetic analysis using non-compartmental analysis with Winnonlin 1.5. The results of the pharmacokinetic parameters analysis for guiafenesin include a $T_{max}$ of 1.48 hr, $C_{max}$ (ng/ml) of 2196, $AUC_{0-12}$(hr*ng/ml) of 8702, $T_{1/2}$ of 1.32 hrs., and an $AUC_{inf}$(hr*ng/ml) of 8732.5. The results of the pharmacokinetic parameters analysis for dextromethorphan include a $T_{max}$ of 5.0 hrs, $C_{max}$ (pg/ml) of 5157, $AUC_{0-12}$(hr*pg/ml) of 74209, $T_{1/2}$ of 7.93 hrs., and an $AUC_{inf}$(hr*pg/ml) of 75016.

Example 10

Two batches of guaifenesin-pseudoephedrine HCl bi-layer tablets, one 600 mg and one 1200 mg, were prepared according to the following composition.

600 mg Guaifenesin/60 mg Pseudoephedrine HCl Tablet

SR Layer Formulation

| Components | Weight per 300,000 tablets (kg) |
|------------|-------------------------------|
| Guaifenesin DC (95%) | 157.90 |
| Pseudoephedrine HCl | 18.0 |
| Hydroxypropyl Methylcellulose (METHOCEL E10M) | 4.50 |
| CARBOPOL 974P, NF | 2.25 |
| FD&C Yellow No. 6 Aluminum Lake (15–18%) | 0.24 |
| Magnesium Stearate | 1.50 |

IR Layer Formulation

| Components | Weight per 300,000 tablets (kg) |
|------------|-------------------------------|
| Guaifenesin DC (95%) | 39.476 |
| Microcrystalline Cellulose (AVICEL PH102) | 22.028 |
| Sodium Starch Glycolate | 5.626 |
| Magnesium Stearate, NF | 0.188 |

1200 mg Guaifenesin/120 mg Pseudoephedrine HCl Tablet

SR Layer Formulation

| Components | Weight per 150,000 tablets (kg) |
|------------|-------------------------------|
| Guaifenesin DC (95%) | 157.89 |
| Pseudoephedrine HCl | 18.00 |
| Hydroxypropyl Methylcellulose (METHOCEL E10M) | 4.50 |
| CARBOPOL 974P, NF | 2.25 |
| FD&C Red No. 40 Aluminum Lake (14–16%) | 0.06 |
| Magnesium Stearate | 1.50 |

IR Layer Formulation

| Components | Weight per 150,000 tablets (kg) |
|------------|-------------------------------|
| Guaifenesin DC (95%) | 39.476 |
| Microcrystalline Cellulose (AVICEL PH102) | 22.028 |
| Sodium Starch Glycolate | 5.626 |
| Magnesium Stearate, NF | 0.188 |

Figure 16:
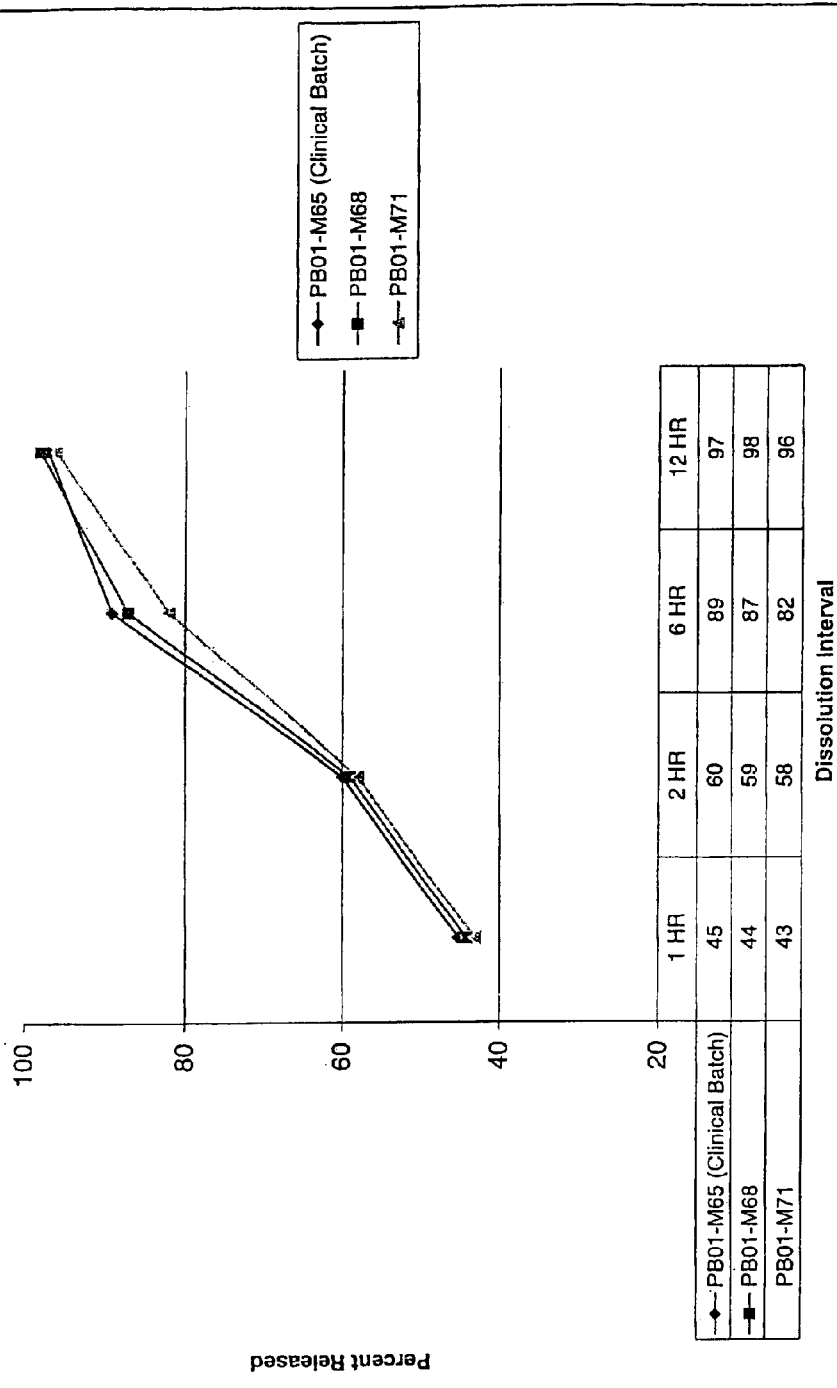
FIG. 16 is a graph demonstrating the dissolution profile of pseudoephedrine HCl in three different batches of a 1200 mg guaifenesin-120 mg pseudoephedrine HCl tablet formulation over a 12 hour period as measured by the percent pseudoephedrine HCl dissolved over time.

The following is a summary of the pseudoephedrine Dissolution Rate of the 1200 mg guaifenesin–60 mg pseu doephedrine tablet results which are also depicted in FIG. 16.

|  | Formulation I<br>% released | Formulation II<br>% released | Formulation III<br>% released |
| --- | --- | --- | --- |
| 1 hr | 45 | 44 | 43 |
| 2 hr | 60 | 59 | 58 |
| 6 hr | 89 | 87 | 82 |
| 12 hr | 97 | 98 | 96 |

The in vivo behavior of the 1200 mg guaifenesin and 120 mg pseudoephedrine tablet was studied by measuring the plasma concentration of guaifenesin, and pseudoephedrine HCl. FIGS. 17–18 illustrate the plasma concentration for each drug (Formulation B and Formulation C) during a 24 hour period. Immediately after administration the plasma concentration of guaifenesin peaks in about an hour, followed by a gradual plasma concentration decrease over 24 hours. Immediately after administration, guaifenesin plasma concentration never decreased below 200 ng/ml over 12 hours. Thereafter, guaifenesin plasma concentration gradually decreased over the next 12 hours. Plasma concentration of pseudoephedrine HCl peaked at about 6 hours and gradually decreased over the next 18 hours. The plasma concentration of pseudoephedrine HCl never decreased to less than 50 ng/ml after 30 minutes of administration.

Example 11

A study was performed to examine the relative bioavailability of sustained release guaifenesin with pseudoephedrine formulations of the present invention in normal, healthy male and/or female volunteers. A batch of guaifenesin and pseudoephedrine bi-layer tablets, 1200 mg, was prepared according to the composition described above for Example 10.

The in vivo behaviors of a 1200 mg tablet administered to volunteers in the fasting state (about 10 hours pre-dose until about 4 hours after dosing) were compared. The open-label study involved 29 healthy volunteers between the ages of 18 and 55. The subjects weighed within 15% of their Ideal Body Weight as defined by the 1983 Metropolitan Life chart. The 29 volunteers were divided into two treatment groups, half receiving the 1200 mg tablet while fasting for Period 1 of the trial. Each volunteer was administered one dose of the appropriate tablet and then monitored over a 16 hour period.

Blood samples (7 ml with sodium heparin as anticoagulant) were taken about one hour prior to dosing and at specific intervals up to 16 hours after dosing (at 0.25, 0.5, 0.75, 1, 1.5, 2, 3, 4, 6, 8, 10, 12, 14, and 16 hours). All blood samples were chilled and centrifuged within 30 minutes of being drawn. The plasma was separated, transferred to a polypropylene tube, frozen at –20° C. or below and stored frozen until being shipped for guaifenesin and pseudoephedrine analysis.

The plasma samples were analyzed by a fully validated HPLC method by PPD Development (3230 Deming Way Suite 190, Middleton, Wis. 53562). The resulting plasma concentration v. time data was subjected to pharmacokinetic analysis using non-compartmental analysis with WinnonlinF 1.5. The results of the pharmacokinetic parameters analysis for guiafenesin include a $T_{max}$ of 1.48 hr, $C_{max}$ (ng/ml) of 2196, $AUC_{0-12}$(hr*ng/ml) of 8702, $T_{1/2}$ of 1.32 hrs., and an $AUC_{inf}$(hr*ng/ml) of 8732.5. The results of the pharmacokinetic parameters analysis for pseudoephedrine include a $T_{max}$ of 6 hrs, $C_{max}$ (ng/ml) of 300, $AUC_{0-12}$(hr*ng/ml) of 4201, $T_{1/2}$ of 5.98 hrs., and an $AUC_{inf}$ (hr*ng/ml) of 4709.

Other embodiments and uses of the invention will be apparent to those of skill in the art from consideration of the specification and practice of the invention disclosed herein. The specification and examples should be considered exemplary only with the true scope and spirit of the invention indicated by the following claims. As will be easily understood by those of skill in the art, variations and modifications of each of the disclosed embodiments can be easily made within the scope of this invention as defined by the following claims.

What is claimed is:

1. A modified release drug product comprising a first quantity of guaifenesin in an immediate release formulation wherein the guaifenesin becomes bioavailable in a subject's stomach; a second quantity of guaifenesin in a release-delaying matrix; and at least one additional drug, wherein the release-delaying matrix comprises a hydrophilic polymer and a water-insoluble polymer in a weight ratio of hydrophilic polymer to water-insoluble polymer from about 1:1 to about 9:1, wherein the immediate release formulation guaifenesin has a $C_{max}$ in a human subject equivalent to the $C_{max}$ obtained when a dose of a standard immediate release formulation having one third the amount of guaifenesin is dosed, and immediately after administration the serum concentration of guaifenesin peaks in about an hour, followed by a gradual serum concentration decrease over twenty-four hours but the serum concentration of guaifenesin never decreases below the minimum concentration of said standard immediate release formulation over twelve hours, and wherein the drug product releases a therapeutically effective bioavailable guaifenesin dose for at least twelve hours after a single dose in the human subject according to serum analysis.

2. The modified release drug product according to claim 1, wherein the hydrophilic polymer is acacia, gum tragacanth, locust bean gum, guar gum, karaya gum, modified cellulosic, methylcellulose, hydroxymethylcellulose, hydroxypropyl methylcellulose, hydroxypropyl cellulose, hydroxyethylcellulose, carboxymethylcellulose, agar, pectin, carrageen, alginate, carboxypolymethylene, gelatin, casein, zein, bentonite, magnesium aluminum silicate, polysaccharide, modified starch derivatives, or a combination thereof.

3. The modified release drug product according to claim 1, wherein the water-insoluble polymer is polyacrylic acid, acrylic resin, acrylic latex dispersion, cellulose acetate phthalate, polyvinyl acetate phthalate, hydroxypropyl methylcellulose phthalate, or a combination thereof.

4. The modified release drug product according to claim 1, wherein the hydrophilic polymer is hydroxypropyl methylcellulose and the water-insoluble polymer is an acrylic resin.

5. The modified release drug product according to claim 1, wherein the immediate release formulation, release-delaying matrix, or both further comprises the at least one additional drug.

6. The modified release drug product according to claim 1, wherein the additional drug is an antitussive, a decongestant, an antihistamine, an analgesic, or combinations thereof.

7. The modified release drug product according to claim 6, wherein the additional drug is dextromethorphan hydrobromide, codeine, hydrocodone, phenylephrine hydrochloride, phenylpropanolamine hydrochloride, pseudoephedrine hydrochloride, ephedrine, chlorpheniramine maleate, brompheniramine maleate, phenindamine tartrate, pyrilamine maleate, doxylamine succinate, phenyltoloxamine citrate, diphenhydramine hydrochloride, promethazine, clemastine fumerate, aspirin, ibuprofen, acetaminophen, naprosin, or combinations thereof.

8. The modified release drug product according to claim 6, wherein the additional drug is dextromethorphan hydrobromide, pseudoephedrine hydrochloride, or a combination thereof.

9. The modified release drug product according to claim 1, further comprising binders, colorants, excipients, glidants, lubricants, preservatives, stabilizers, surface active agents, or combinations thereof.

10. The modified release drug product according to claim 9, wherein the lubricant is magnesium stearate, calcium stearate, zinc stearate, powdered stearic acid, hydrogenated vegetable oil, talc, polyethylene glycol, mineral oil, or a combination thereof.

11. The modified release drug product according to claim 9, wherein the binder is sucrose, lactose, gelatin, starch paste, acacia, tragacanth, povidone, polyethylene glycol, Pullulan, corn syrup, or a combination thereof.

12. The modified release drug product according to claim 9, wherein the glidant is colloidal silicon dioxide, talc, or a combination thereof.

13. The modified release drug product according to claim 9, wherein the surface active agent is sodium lauryl sulfate, dioctyl sodium sulfosuccinate, triethanolamine, polyoxyethylene sorbitan, poloxalkol, quaternary ammonium salts, or a combination thereof.

14. The modified release drug product according to claim 9, wherein the excipient is mannitol, glucose, fructose, xylose, galactose, maltose, xylitol, sorbitol, potassium chloride, potassium sulfate, potassium phosphate, sodium chloride, sodium sulfate, sodium phosphate, magnesium chloride, magnesium sulfate, magnesium phosphate, microcrystalline cellulose, sodium starch glycolate, or a combination thereof.

15. The modified release drug product according to claim 9, wherein the colorant is Emerald Green Lake, FD&C Red #40, FD&C Yellow #6, FD&C Yellow #10, FD&C Blue #1, or a combination thereof.

16. The modified release drug product according to claim 1, wherein the immediate release formulation further comprises microcrystalline cellulose, sodium starch glycolate, and magnesium stearate.

17. The modified release drug product according to claim 1, wherein a total quantity of guaifenesin is from about 600 mg to about 1200 mg.

18. The modified release drug product according to claim 1, wherein a ratio of a total quantity of guaifenesin to the additional drug is from about 1:1 to about 4:1 by weight.

19. The modified release drug product according to claim 1, wherein a ratio of a total quantity of guaifenesin to the additional drug is from about 3:2 to about 9:1 by weight.

20. The modified release drug product according to claim 1 or 17, wherein a ratio of the first quantity of guaifenesin to the second quantity of guaifenesin is about 1:1 to about 1:49 by weight.

21. The modified release drug product according to claim 1 or 17, wherein a ratio of the first quantity of guaifenesin to the second quantity of guaifenesin is from about 2:3 to about 1:19.

22. The modified release drug product according to claim 17, wherein guaifenesin has a $C_{max}$ of at least about 1900 ng/ml and an $AUC_{inf}$ of at least 7000 hr*ng/ml.

23. The modified release drug product according to claim 17, wherein guaifenesin has a $C_{max}$ of at least 1000 ng/ml and an $AUC_{inf}$ of at least 3500 hr*ng/ml.

24. The modified release drug product according to claim 1, wherein the guaifenesin has a half life of at least 3 hours as determined by serum analysis.

25. The modified release drug product according to claim 1, wherein the release-delaying matrix comprises about 75% to about 95% by weight of guaifenesin, from about 1% to about 15% of the additional drug, from about 1% to about 10% of the hydrophilic polymer, and about 0.5% to about 2.5% of the water-insoluble polymer by weight.

26. The modified release drug product according to claim 1, wherein the immediate release formulation and the release-delaying matrix each comprise abutting substantially planar layers which form a bilayer tablet.

27. The modified release drug product according to claim 1, wherein the release-delaying matrix is coated by a layer of the immediate release formulation.

28. The modified release drug product according to claim 17, wherein the release-delaying matrix comprises from about 80% to about 90% by weight of guaifenesin, from about 3% to about 10% by weight of the additional drug, from about 2% to about 5% of the hydrophilic polymer, and from about 1% to about 1.5% by weight of the water-insoluble polymer.

29. A modified release drug product comprising a first quantity of guaifenesin in an immediate release formulation wherein the guaifenesin becomes bioavailable in a subject's stomach; a second quantity of guaifenesin in a sustained release form,
  wherein the sustained release form comprises a hydrophilic polymer and a water-insoluble polymer in a weight ratio of hydrophilic polymer to water-insoluble polymer from about 1:1 to about 9:1,
  wherein the immediate release formulation guaifenesin has a $C_{max}$ in a human subject equivalent to the $C_{max}$ obtained when a dose of a standard immediate release formulation having one third the amount of guaifenesin is dosed, and immediately after administration the serum concentration of guaifenesin peaks in about an hour, followed by a gradual serum concentration decrease over twenty-four hours but the serum concentration of guaifenesin never decreases below the minimum concentration of said standard immediate release formulation over twelve hours, and
  wherein the drug product releases a therapeutically effective bioavailable guaifenesin dose for at least twelve hours after a single dose in the human subject according to serum analysis.

30. The modified release drug product according to claim 29, wherein a total quantity of guaifenesin is from about 600 mg to about 1200 mg.

31. The modified release drug product of claim 30, wherein a ratio of the first quantity of guaifenesin to the second quantity of guaifenesin is about 1:1 to about 1:49.

32. The modified release drug product of claim 30, wherein a ratio of the first quantity of guaifenesin to the second quantity of guaifenesin is about 2:3 to about 1:19.

33. The modified release drug product according to claim 30, wherein guaifenesin has a $C_{max}$ from about 1600 to 2500 ng/ml and an $AUC_{inf}$ of about 5600 to 8750 hr*ng/ml.

34. The modified release drug product according to claim 30, wherein the guaifenesin has a $C_{max}$ of at least 1900 ng/ml and an $AUC_{inf}$ of at least 7000 hr*ng/ml.

35. The modified release drug product according to claim 30, wherein the guaifenesin has a $C_{max}$ of about 800 to 1250 ng/ml and an $AUC_{inf}$ of about 2800 to 4375 hr*ng/ml.

36. The modified release drug product according to claim 30, wherein the guaifenesin has a $C_{max}$ of at least 1000 ng/ml and an $AUC_{inf}$ of at least 3500 hr*ng/ml.

37. The modified release drug product according to claim 29, wherein the guaifenesin has a half life of at least three hours as determined by serum analysis.

38. The modified release drug product according to claim 29, wherein the immediate release formulation and the sustained release form each comprise abutting substantially planar layers which form at bilayer tablet.

39. The modified release drug product according to claim 29, wherein the sustained release form is coated by a layer of the immediate release formulation.

40. The modified release drug product according to claim 29, wherein the drug product is shaped as a capsule and contains the immediate release formulation and the sustained release form.

41. The modified release drug product according to claim 29, wherein the drug product is approximately equally effective when administered to the human subject with an empty or full stomach.

42. The modified release drug product according to claim 30, wherein the drug product has a guaifenesin serum concentration profile of FIG. 10.

43. A modified release drug product comprising a first quantity of guaifenesin in an immediate release formulation wherein the guaifenesin becomes bioavailable in a subject's stomach; a second quantity of guaifenesin in a sustained release formulation; and at least one additional drug,
wherein the sustained release formulation comprises a hydrophilic polymer and a water-insoluble polymer in a weight ratio of hydrophilic polymer to water-insoluble polymer from about 1:1 to about 9:1,
wherein the ratio of the first quantity to the second quantity of guaifenesin is about 1:1 to about 1:49,
wherein the immediate release formulation guaifenesin has a $C_{max}$ in a human subject equivalent to the $C_{max}$ obtained when a dose of a standard immediate release formulation having one third the amount of guaifenesin is dosed, and immediately after administration the serum concentration of guaifenesin peaks in about an hour, followed by a gradual serum concentration decrease over twenty-four hours but the serum concentration of guaifenesin never decreases below the minimum concentration of said standard immediate release formulation over twelve hours, and
wherein the drug product provides a therapeutically effective bioavailable guaifenesin dose for at least twelve hours after a single dose in the human subject according to serum analysis.

44. The modified release drug product according to claim 43, wherein a total quantity of guaifenesin is from about 600 mg to about 1200 mg.

45. The modified release drug product according to claim 43, wherein the additional drug is an antitussive, decongestant, antihistamine, analgesic, or combinations thereof.

46. The modified release drug product according to claim 45, wherein the additional drug is dextromethorphan hydrobromide, codeine, hydrocodone, phenylephrine hydrochloride, phenylpropanolamine hydrochloride, pseudoephedrine hydrochloride, ephedrine, chlorpheniramine maleate, brompheniramine maleate, phenindamine tartrate, pyrilamine maleate, doxylamine succinate, phenyltoloxamine citrate, diphenhydramine hydrochloride, promethazine, clemastine fumerate, acetaminophen, aspirin, ibuprofen, naprosin, or combinations thereof.

47. The modified release drug product according to claim 45, wherein the additional drug is dextromethorphan hydrobromide, pseudoephedrine hydrochloride, or a combination thereof.

48. The modified release drug product according to claim 43, wherein a ratio of a total quantity of guaifenesin to the additional drug is from about 1:1 to about 4:1 by weight.

49. The modified release drug product according to claim 43, wherein a ratio of a total quantity of guaifenesin to the additional drug is from about 3:2 to about 9:1 by weight.

50. The modified release drug product according to claim 43 or 49, wherein a ratio of the first quantity of guaifenesin to the second quantity of guaifenesin is from about 2:3 to about 1:19.

51. The modified release drug product according to claim 44, wherein a guaifenesin $C_{max}$ of the drug product is from about 1600 to 2500 ng/ml and an $AUC_{inf}$ is from about 5600 to 8750 hr*ng/ml.

52. The modified release drug product according to claim 44, wherein a guaifenesin $C_{max}$ is at least 1900 ng/ml and an $AUC_{inf}$ is at least 7000 hr*ng/ml.

53. The modified release drug product according to claim 44, wherein a guaifenesin $C_{max}$ is about 800 to 1250 ng/ml and an $AUC_{inf}$ is from about 2800 to 4375 hr*ng/ml.

54. The modified release drug product according to claim 44, wherein a guaifenesin $C_{max}$ is at least 1000 ng/ml and an $AUC_{inf}$ is at least 3500 hr*ng/ml.

55. The modified release drug product according to claim 43, wherein the guaifenesin has a half life of at least three hours as determined by serum analysis.

56. The modified release drug product according to claim 43, wherein the immediate release formulation and the sustained release formulation each comprise abutting substantially planar layers which form a bilayer tablet.

57. The modified release drug product according to claim 43, wherein the sustained release formulation is coated by a layer of the immediate release formulation.

58. The modified release drug product according to claim 43, wherein the drug product is shaped as a capsule containing the immediate release formulation and the sustained release formulation.

59. The modified release drug product according to claim 43, wherein the drug product is approximately equally effective when administered to the human subject with an empty or full stomach.

60. The modified release drug product according to claim 44, wherein the drug product has the serum guaifenesin concentration profile of FIG. 10.

61. A method of treating coughing and symptoms or diseases associated with coughing which comprises administering to a subject in need of such treatment a therapeutically effective amount of a modified release drug product according to claim 1, 43 or 29 effective to treat coughing and symptoms or diseases associated with coughing in the subject.

62. The method according to claim 61, wherein the drug product is administered orally.

63. The method according to claim 61, wherein the additional drug is an antitussive, a decongestant, an antihistamine, an analgesic, or combinations thereof.

64. The method according to claim 63, wherein the additional drug is dextromethorphan hydrobromide, codeine, hydrocodone, phenylephrine hydrochloride, phenylpropanolamine hydrochloride, pseudoephedrine hydrochloride, ephedrine, chlorpheniramine maleate, brompheniramine maleate, phenindamine tartrate, pyrilamine maleate, doxylamine succinate, phenyltoloxamine citrate, diphenhydramine hydrochloride, promethazine, clemastine fumerate, aspirin, ibuprofen, acetaminophen, naprosin, or combinations thereof.

65. The method according to claim 63, wherein the additional drug is dextromethorphan hydrobromide, pseudoephedrine hydrochloride, or a combination thereof.

66. The method according to claim 61, wherein a total quantity of guaifenesin is from about 600 mg to about 1200 mg.

67. The method according to claim 61, wherein a ratio of a total quantity of guaifenesin to the additional drug is from about 1:1 to about 4:1 by weight.

68. The method according to claim 61, wherein a ratio of the first quantity of guaifenesin to the second quantity of guaifenesin is about 1:1 to about 1:49 by weight.

69. The method according to claim 61, wherein guaifenesin has a $C_{max}$ of at least about 1900 ng/ml and an $AUC_{inf}$ of at least 7000 hr*ng/ml.

70. A method of treating coughing and symptoms or diseases associated with coughing which comprises administering to a subject in need of such treatment a therapeutically effective amount of a modified release drug product having a first quantity of guaifenesin in an immediate release formulation which becomes fully bioavailable in a subject's stomach and a second quantity of guaifenesin in a release-delaying matrix comprising a hydrophilic polymer and a water-insoluble polymer wherein a weight ratio of said hydrophilic polymer to said water-insoluble polymer is in a range of from about 1:1 to about 6:1, wherein said immediate release formulation guaifenesin demonstrates a $C_{max}$ in a human subject equivalent to the $C_{max}$ obtained when a dose of a standard immediate release formulation having one third the amount of guaifenesin is dosed, and immediately after administration the serum concentration of guaifenesin peaks in about an hour, followed by a gradual serum concentration decrease over twenty-four hours but the serum concentration of guaifenesin never decreases below the minimum concentration of said standard immediate release formulation over twelve hours, and wherein said drug product provides therapeutically effective bioavailability for at least twelve hours after a single dose in the human subject according to serum analysis.

71. The method according to claim 70, wherein the drug product is administered orally.

72. The method according to claim 70, wherein a ratio of the first quantity of guaifenesin to the second quantity of guaifenesin is about 1:1 to about 1:49 by weight.

73. The method according to claim 70, wherein guaifenesin has a $C_{max}$ of at least about 1900 ng/ml and an $AUC_{inf}$ of at least 7000 hr*ng/ml.

74. The modified release drug product according to claim 1 or 43, wherein a ratio of a total quantity of guaifenesin to the additional drug is from about 3:1 to about 20:1 by weight.

75. The modified release drug product according to claim 1 or 43, wherein the guaifenesin has a half life of at least 1.3 hours as determined by serum analysis.

76. The modified release drug product according to claim 43, wherein the immediate release formulation, sustained release formulation, or both comprises the at least one additional drug.

77. The method according to claim 61, wherein a ratio of a total quantity of guaifenesin to the additional drug is from about 3:1 to about 20:1 by weight.

* * * * *